United States Patent
Charlot et al.

(10) Patent No.: US 7,693,917 B2
(45) Date of Patent: **\*Apr. 6, 2010**

(54) METHOD FOR ADAPTIVE DATA MANAGEMENT

(75) Inventors: Regis Charlot, Lake Bluff, IL (US);
Frank Naeymi-Rad, Libertyville, IL (US); Alina Oganesova, Chicago, IL (US); Jose Maldonado, Chicago, IL (US); David Oran Haines, Norridge, IL (US)

(73) Assignee: Intelligent Medical Objects, Inc., Northbrook, IL (US)

( * ) Notice: Subject to any disclaimer, the term of this patent is extended or adjusted under 35 U.S.C. 154(b) by 400 days.

This patent is subject to a terminal disclaimer.

(21) Appl. No.: 11/065,600

(22) Filed: Feb. 24, 2005

(65) Prior Publication Data

US 2005/0216503 A1 Sep. 29, 2005

Related U.S. Application Data

(63) Continuation-in-part of application No. 09/997,723, filed on Nov. 30, 2001, now Pat. No. 6,904,432.

(51) Int. Cl.
*G06F 7/00* (2006.01)
*G06F 17/00* (2006.01)

(52) U.S. Cl. .................................. 707/804; 707/811

(58) Field of Classification Search ............... 707/102
See application file for complete search history.

(56) References Cited

U.S. PATENT DOCUMENTS

| | | | |
|---|---|---|---|
| 5,748,872 A | 5/1998 | Norman | |
| 5,819,257 A | 10/1998 | Monge et al. | |
| 5,903,889 A | 5/1999 | Huerga | |
| 5,931,900 A * | 8/1999 | Notani et al. | 709/201 |
| 6,006,233 A | 12/1999 | Schultz | |
| 6,029,162 A | 2/2000 | Schultz | |
| 6,078,924 A * | 6/2000 | Ainsbury et al. | 707/101 |
| 6,105,035 A | 8/2000 | Monge et al. | |
| 6,115,715 A | 9/2000 | Traversat | |
| 6,122,636 A | 9/2000 | Malloy | |
| 6,167,406 A * | 12/2000 | Hoskins et al. | 707/102 |
| 6,192,371 B1 | 2/2001 | Schultz | |
| 6,345,278 B1 * | 2/2002 | Hitchcock et al. | 707/100 |

(Continued)

OTHER PUBLICATIONS

Schultz, Adept-The Advanced Database Environment for Planning and Tracking, Jul.-Sep. 1998, Bell Labs Technical Journal, Lucent Technologies p. 1 and 4. (7 pgs).

(Continued)

*Primary Examiner*—John R. Cottingham
*Assistant Examiner*—Mariela D Reyes
(74) *Attorney, Agent, or Firm*—Beem Patent Law Firm

(57) ABSTRACT

A method for managing a back-end information storage infrastructure and a flexible development environment for data storage using a computer system. The method includes managing system resources including a relational database. Meta data models are created to model processes and to define meta data elements and their relationships by using trees and graphs. The method manages access to the data by authenticating users through several levels of authentication describing user rights, while providing management of multi-user access and concurrency. The method includes running the processes that generate instance data, storing the instance data following the meta data model, and transforming the instance data into physical views.

27 Claims, 15 Drawing Sheets

U.S. PATENT DOCUMENTS

| | | | |
|---|---|---|---|
| 6,643,652 | B2 | 11/2003 | Helgeson et al. |
| 6,662,188 | B1 * | 12/2003 | Rasmussen et al. ......... 707/102 |
| 6,708,186 | B1 | 3/2004 | Calborn et al. |
| 6,721,747 | B2 | 4/2004 | Lipkin |
| 2001/0051880 | A1 | 12/2001 | Schurenberg |
| 2002/0007284 | A1 | 1/2002 | Schurenberg |
| 2002/0010679 | A1 * | 1/2002 | Felsher ........................ 705/51 |
| 2002/0169788 | A1 * | 11/2002 | Lee et al. ................. 707/104.1 |

OTHER PUBLICATIONS

Meyers, The Follow-up Note, AMIA Conference, Los Angeles, CA, Nov. 6, 2000, Intelligent Medical Objects.

Kepic, Abstractor, Version 1.1.1 Production Release, Intelligent Medical Objects, Inc., Oct. 1999.

QuadrMed Production Release CD, Northbrook, IL (1pg) 9.

Pilkington, Abstractor + Database Design, V.1.2., Internal use only documents delivered with QuadraMed Production Release, under nondisclosure agreement, pursuant to sale of Abstractor + Version 1.1.1, pp. 6-9, 14. (103 pgs) Jul. 1999.

Többicke, Distributed File Systems: Focus on Andrew File System/ Distributed File Service (AFS/DFS), Thirteenth IEEE Symposium on Mass Storage Systems, 1994, pp. 23-26, 1054-9173194, European Laboratory for Particle Physics (CERN), Geneva, Switzerland (4 pgs).

Ellison, Introduction to SQL, booklet, 1989, Oracle Corporation, USA.

* cited by examiner

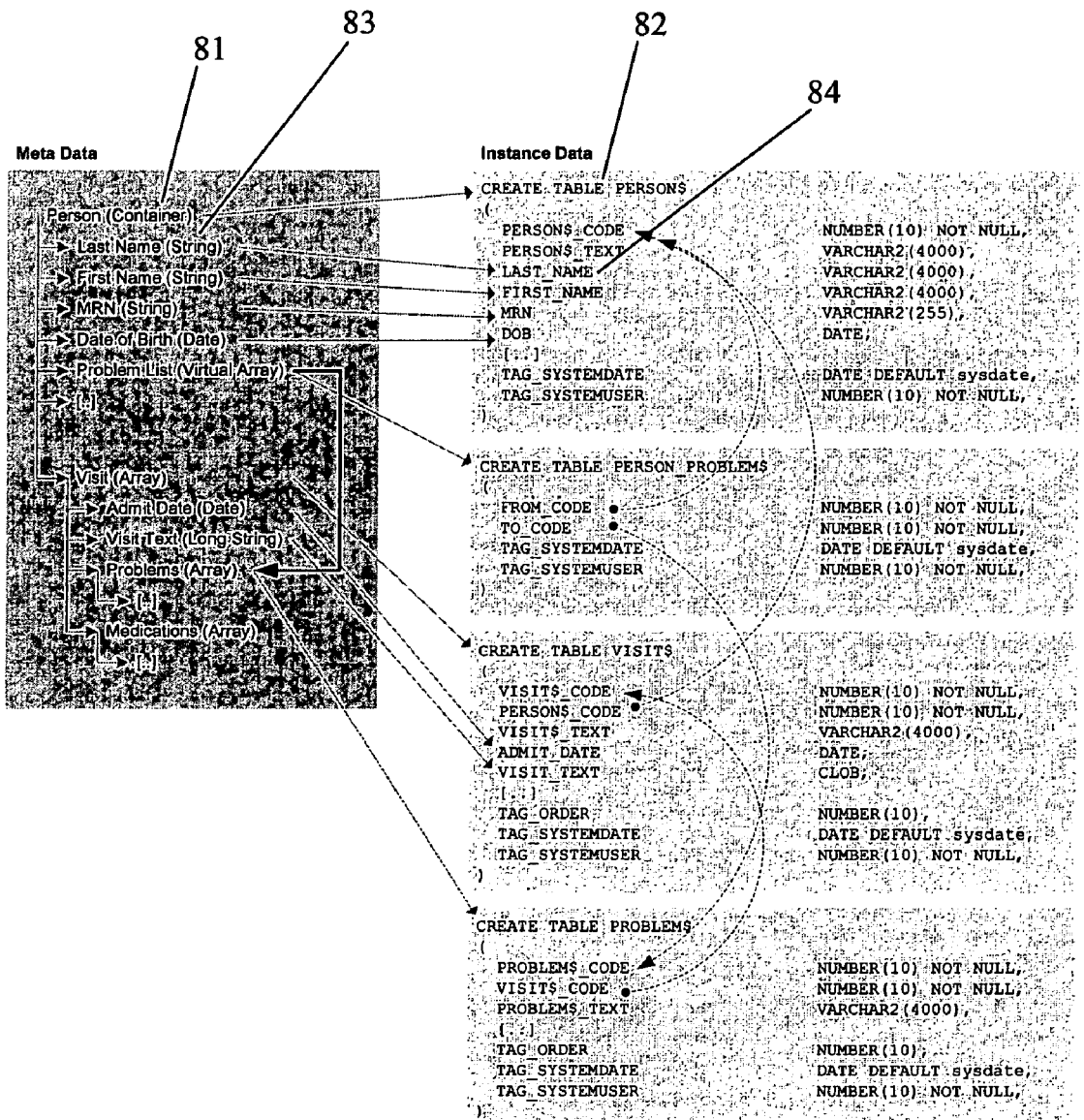
FIG. 10-B

METHOD FOR ADAPTIVE DATA MANAGEMENT

CROSS-REFERENCE TO RELATED APPLICATION

This application is a continuation-in-part of U.S. application Ser. No. 09/997,723 filed on Nov. 30, 2001 now U.S. Pat. No. 6,904,432.

BACKGROUND OF THE INVENTION

1. Field of the Invention

The field of invention is data management, including information storage infrastructure and database application development environments, for use with relational databases.

2. Description of the Related Art

Until now, efforts to create data management systems and software for databases have involved extremely lengthy and costly development cycles for database design, implementation, tuning and maintenance. These problems have been all too typical in the design and specification of database schemas for projects.

Data warehousing is a common method of recording of an enterprise's past transactional and operational activities, stored in a database. Data warehouses often hold large amounts of information which are sometimes subdivided into smaller logical units called dependent data marts. Data warehousing projects have involved complex, time-consuming and expensive phases including data cleansing, building a database dimensional model such as a snowflake model or the like, and harvesting reports. The first phase, data cleansing, typically represents over 80% of the total time required for such data warehousing projects.

Data cleansing is the process of amending or removing data in a database that is incorrect, incomplete, improperly formatted, or duplicated. An organization in a data-intensive field like banking, insurance, retailing, telecommunications, or transportation might use a data scrubbing tool to systematically examine data for flaws by using rules, algorithms, and look-up tables. Typically, a database scrubbing tool includes programs that are capable of correcting a number of specific type of mistakes, such as adding missing zip codes or finding duplicate records. Using a data scrubbing tool can save time over fixing errors manually, but data scrubbing tools are costly and still require significant amounts of time to implement. Due to the nature of ADM data storage and the metadata model it utilizes, the data requires little or no cleansing before inclusion into a data warehousing database.

Tree data storage refers to data elements having only one parent data element. On the other hand, graph data storage refers to data elements that may have more than one parent data element. Graph data storage commonly results when the data stored within a databases requires complex relationships in order to be used in a particular application. The more a data solution is graph-like, the more likely it is to suffer from performance and efficiency problems. There are very few practical solutions to graph data storage that fully address graph data storage side effects. Further, many important database applications, for example patient medical record applications, require graph-like data solutions. Typically, solutions to such problems are arrived at on an ad hoc basis, whereby one or more development teams will customize a solution to address a particular application problem. The problem with such an ad hoc approach is that it leads to ossification—future changes to the data storage infrastructure, either to implement a fix or to enhance the system, require another exhaustive database development effort, which is both costly and time-consuming.

What is needed is a data management method that will address the issues presented above.

SUMMARY OF THE INVENTION

The inventive advanced data management method and system are capable of use with relational database management systems (RDBMS or "relational databases"), web site and client-server applications, document and knowledge management applications, discrete data storage, and object-oriented databases. The invention is particularly useful when used with relational databases for data management and application development.

In accordance with one aspect of the invention, a method for managing an information storage infrastructure and a flexible development environment for data storage using a computer system, comprisies managing system resources including a relational database; authenticating and selectively providing access to users through predetermined user roles; creating a metadata model having metadata elements and relationships among the elements using trees and graphs in a table driven infrastructure; running the processes and generating instance data; storing the instance data in a plurality of tables having said table driven infrastructure within said relational database; and performing transforms of the instance data.

In accordance with another aspect of the invention, a method for managing instance data, comprises defining a metadata model establishing metadata elements and a table driven infrastructure for storing the instance data, storing said metadata and said instance data in a relational database, altering said metadata model when necessary without requiring reorganization or substantial manipulation of said instance data, creating a user interface, managing access to said instance data by users based on a security scheme, said managing including allowing authorized users to modify said instance data using a computer through said user interface.

In accordance with another aspect of the invention, a method of managing electronic records, comprises storing data on a relational database; running an application server; authenticating and selectively providing access to users through a directory describing predetermined user rights; rendering data from said relational database, and allowing users to modify data stored on said relational database.

BRIEF DESCRIPTION OF THE SEVERAL VIEWS OF THE DRAWINGS

FIG. 10-B is a schematic illustrating that metadata elements of varying data-types create different instance data storage infrastructure components.

DETAILED DESCRIPTION OF THE INVENTION

1.—ADM

The present invention provides both a back-end information storage infrastructure and a flexible development environment providing a simple component interface to complex back-end data storage. The present invention may also be conceptualized as a role-based enterprise application server, whereby administrators and end-users respectively manage and access the application (and thus the back-end data) through a role-based security scheme. It is an object of the invention to provide a method and system for developing software and managing data while avoiding or minimizing lengthy and costly development cycles for database design, implementation, tuning and maintenance, data cleansing, building of database dimensional models such as snowflake models or the like, and difficulties in harvesting data and generating reports and user screens. ADM thus may be though of as managing complexity; it may organize large and complex data repository structures and generally may simplify their maintenance and administration.

1.1—ADM and Data Management

Figure 1:
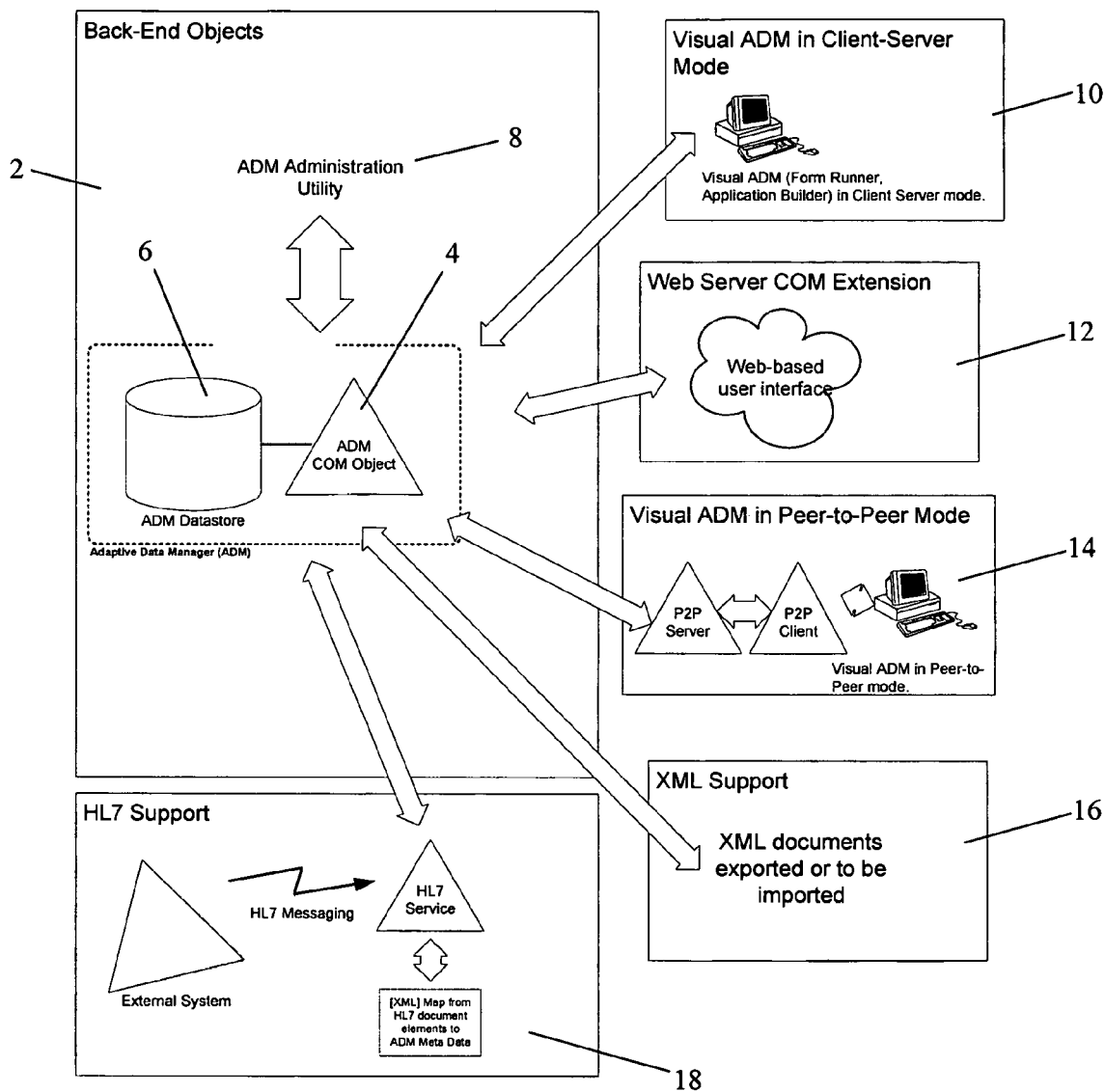
FIG. 1 is a schematic of the inventive adaptive database management component interfaces.

Turning to FIG. 1, Adaptive Data Manager (ADM) is shown in an implementation context. The server side components of ADM 2 include the ADM datastore that is stored on a relational database 6, the ADM component model object (COM) object 4 which may handle all communication with the ADM datastore, and ADM administration utility 8 which may handle management of the ADM datastore with the ADM COM object. The ADM may communicate with an administration utility running on a personal computer vis-á-vis VisualADM in client-server mode 10, in a peer to peer mode 14, or as a web based user interface 12. Support for other external interfaces, such as HL7 messaging services 18, also may be included. HL7 delivers a messaging standard that enables disparate healthcare applications to exchange keys sets of clinical and administrative data.

Extensible markup language describes a class of data representation called XML documents and partially describes the behavior of computer programs which process them. XML is an application profile or restricted form of standard generalized markup language (SGML). By construction, XML documents are conforming SGML documents. In other words, XML enables any storage of information into a text file format for example, as a document. XML databases allow discrete storage of such documents. As shown in FIG. 1, ADM may allow the import and export of many classes of data to and from ADM using XML 16. These classes of data may include user data, ADM metadata, ADM meta views, dictionaries, instance data, and configuration and application scripts. The instance data XML document type definition is drivenby the metadata definition.

ADM is designed as an integrated, role-based enterprise application server. ADM integrates the parts necessary to develop and deploy an application, or a suite of applications, within an enterprise and integrates role-based access to the different parts. In other words, all elements of ADM, including central data storage, user and security management, knowledge and dictionary management, and application script management, are designed to provide integrated functions and services.

Figure 2:
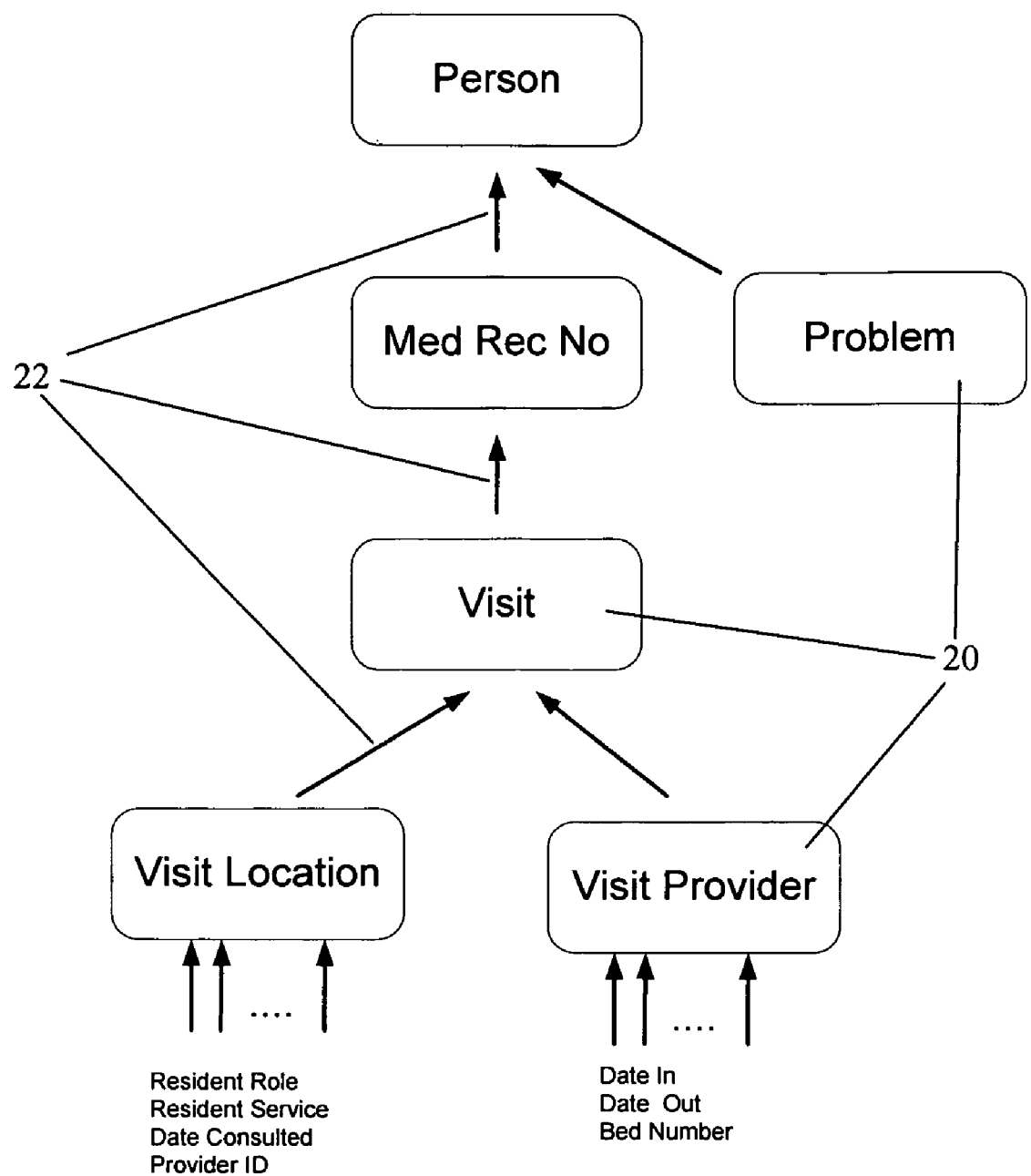
FIG. 2 is a schematic showing metadata defining a pattern for instance data.

In accordance with the inventive ADM method, a database model is provided and is optimized for managing large amounts of data that may have complex interrelationships with a standard front-end component interface. The method thus simplifies database design and data access while reducing development cost and development time. Furthermore, ADM may reduce database administration costs because the database model does not require a large number of qualified technical personnel to monitor all database activity—the data to be collected is described, both in format and in relationships, as a metadata model. FIG. 2 illustrates an example of a metadata model, which is comprised of metadata elements 20 and relationships among the metadata elements. As seen in FIG. 2, the relationships between metadata elements represent associations found in a real-world environment.

Figure 3:
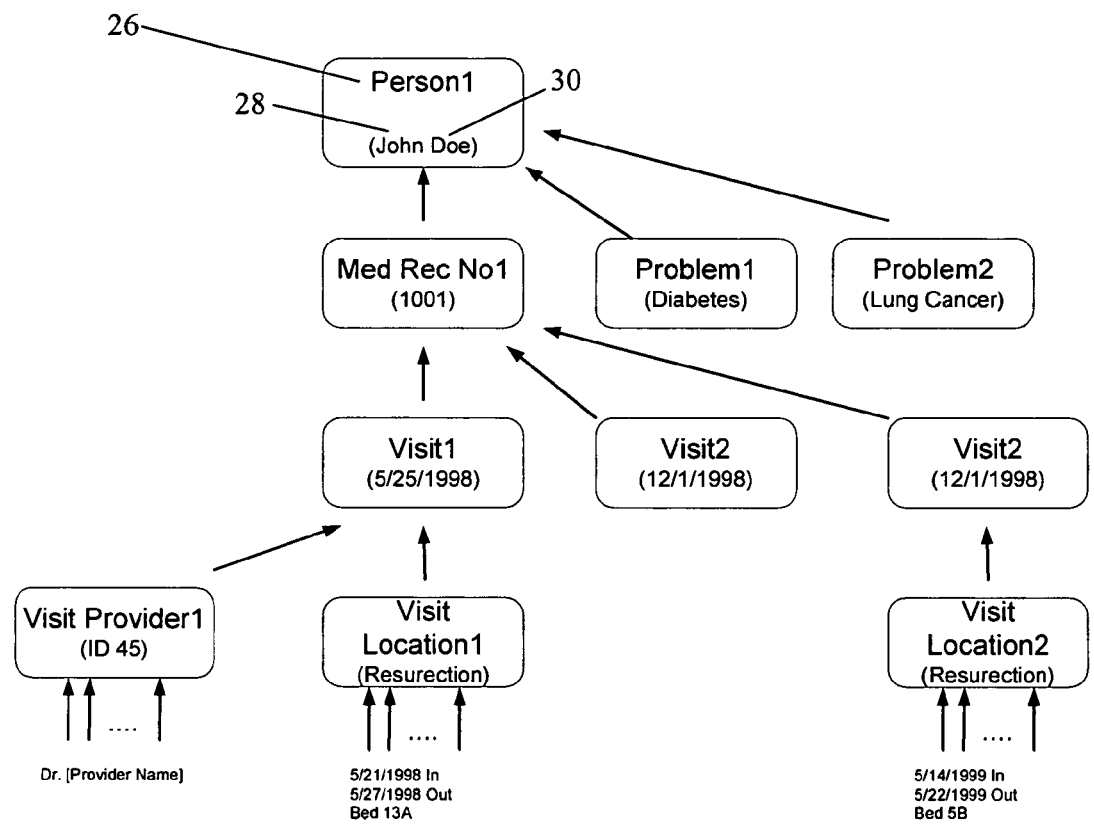
FIG. 3 is a schematic of instance data infrastructure following a metadata pattern.

FIG. 3 illustrates user data, or instance data, which may be collected and stored using the format defined by the metadata. In other words, the metadata model manages the pattern of the data, and the instance data that is gathered through a given application utilizing ADM follows that pattern. This is shown in FIG. 3, whereby what previously existed as a metadata element is given actual values in the form of fields within table records. For example, there may be a record 26 within a table named "Person1," and that record may consist of a first name field 28 and a last name field 30.

Metadata thus refers to the organization, or the "patterning," of the actual (or instance) data. In other words, metadata describes the organization of the instance data to ADM, prior to any access or modification (add, delete, or change) of the instance data. Metadata and instance data in turn may be stored in the form of a tree whereby each data element has at most one parent data element, or as a graph whereby each data element may have one or more parent data elements.

Figure 4:
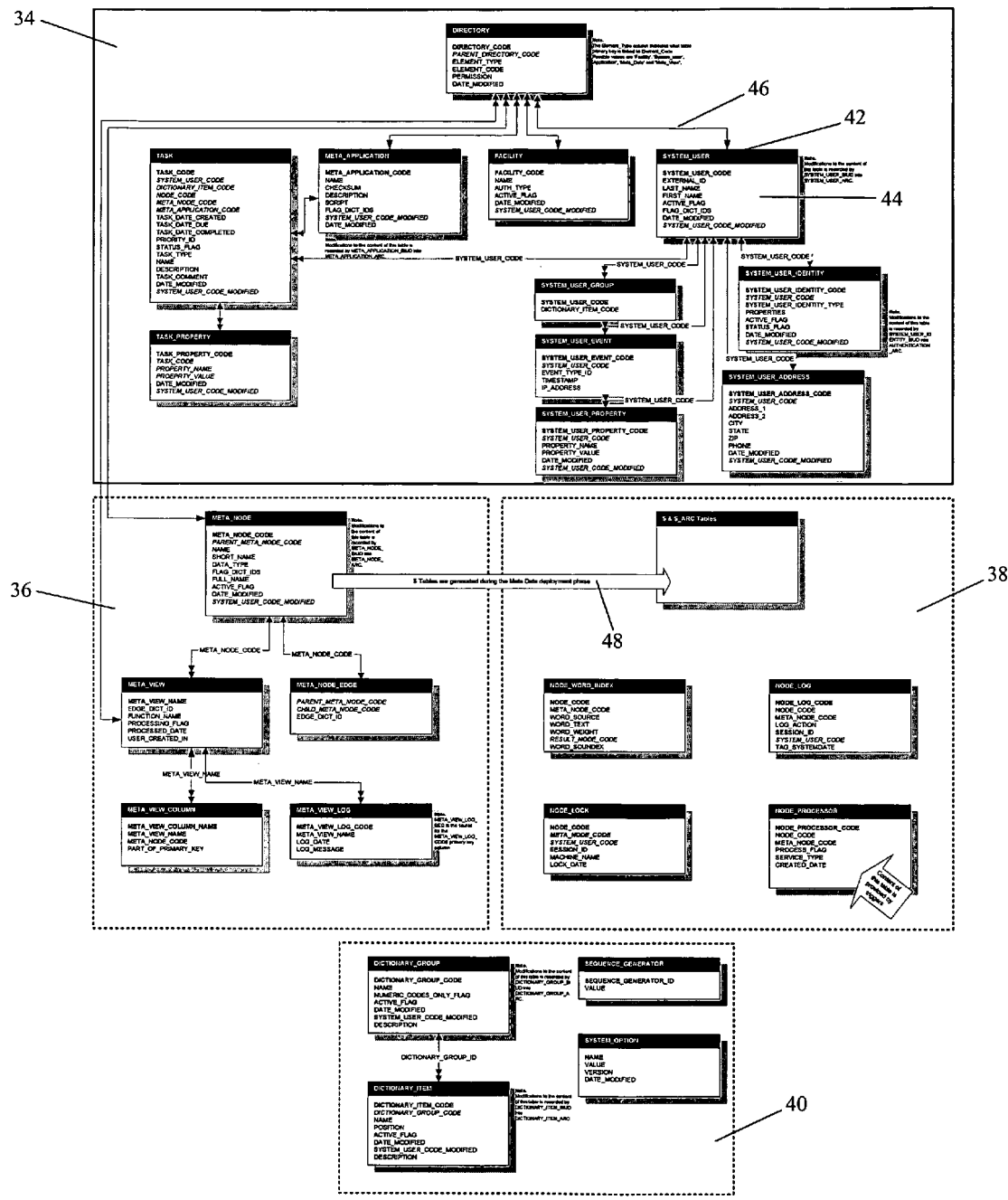
FIG. 4 is a schematic of an entity-relationship diagram that illustrates the ADM database model.

Turning to FIG. 4, a schematic overview of the database design for ADM is shown. The database is comprised of tables 42 which are further comprised of table columns 44 that house data. The four main portions of the database include tables used for user role management 34, metadata management 36, instance data management 38, and miscellaneous system support 40. Relationships between the tables may be in form of foreign or primary keys, constraints, or the like, and are schematically represented by arrows 46. A base set of ADM system tables are created at installation of the back end of ADM, while meta data defined tables are created and managed when the meta data is committed to the database and deployed.

Figure 6:
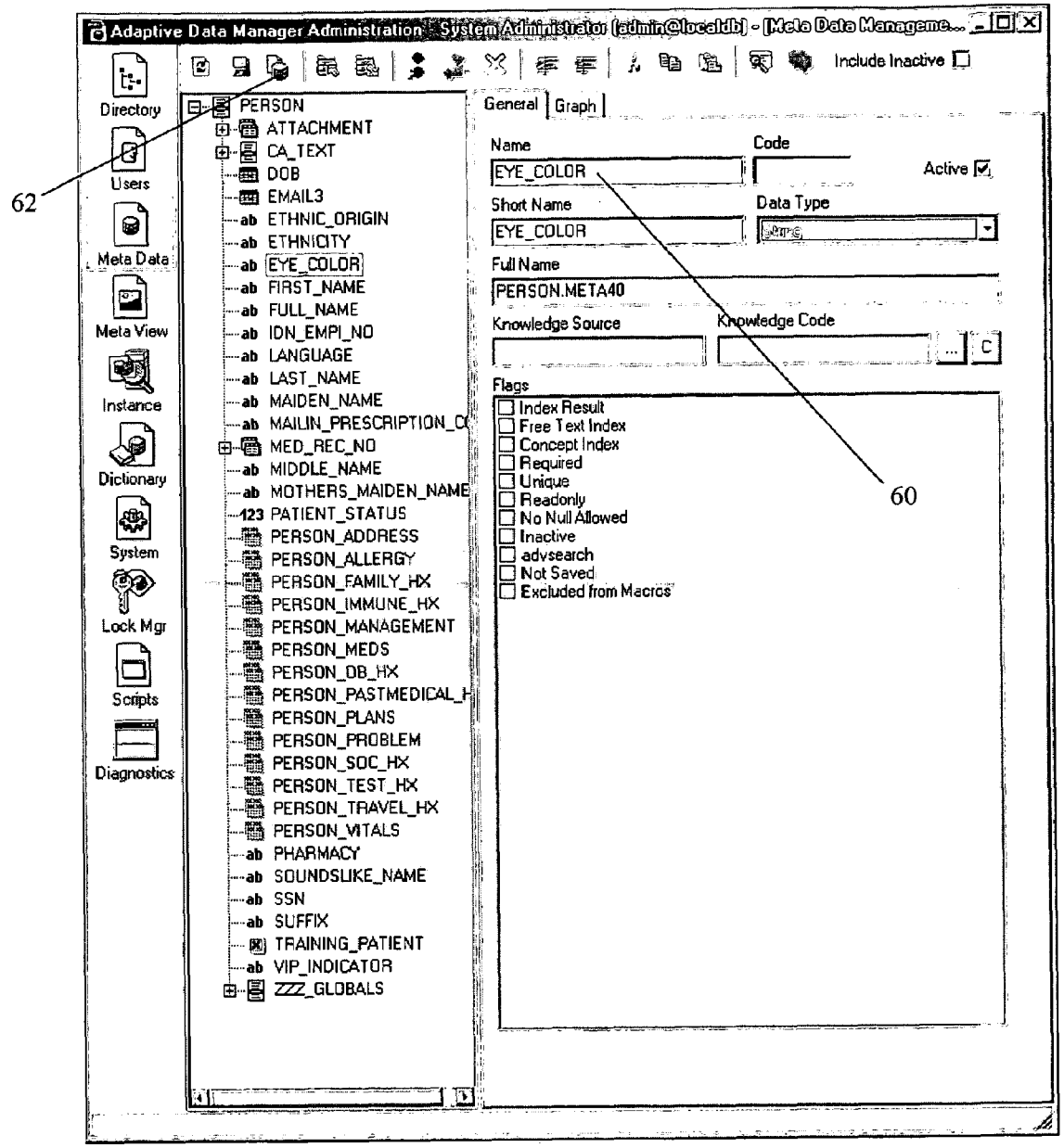
FIG. 6 is a screen of ADM Administration Utility Metadata Manager allowing for the addition of a metadata element.

The inventive method has shown success in managing large numbers of records and in document indexing, making it useful in both traditional client-server implementations and web applications. This is because ADM's use of the metadata model may increase vastly the manageability of the data storage infrastructure by abstracting the definition of the instance data's structure onto a metadata "layer." Since ADM's metadata layer manages and deploys changes to the instance data storage infrastructure—indeed the metadata layer deploys the instance data infrastructure in the first instance—changes made to instance data storage (either by necessity or for enhancement purposes) are much less complex and are achieved with much greater speed than they would be otherwise. As shown in FIG. 6, if, for example, an administrator wishes to create a field for "eye color" in the instance database tables, she may first add the EYE_COLOR metadata element 60. Once the EYE_COLOR data element is saved to the metadata, the administrator then may deploy the new data element to the instance data storage infrastructure (or back-end database for short) using the deployment icon 62.

Figure 7:
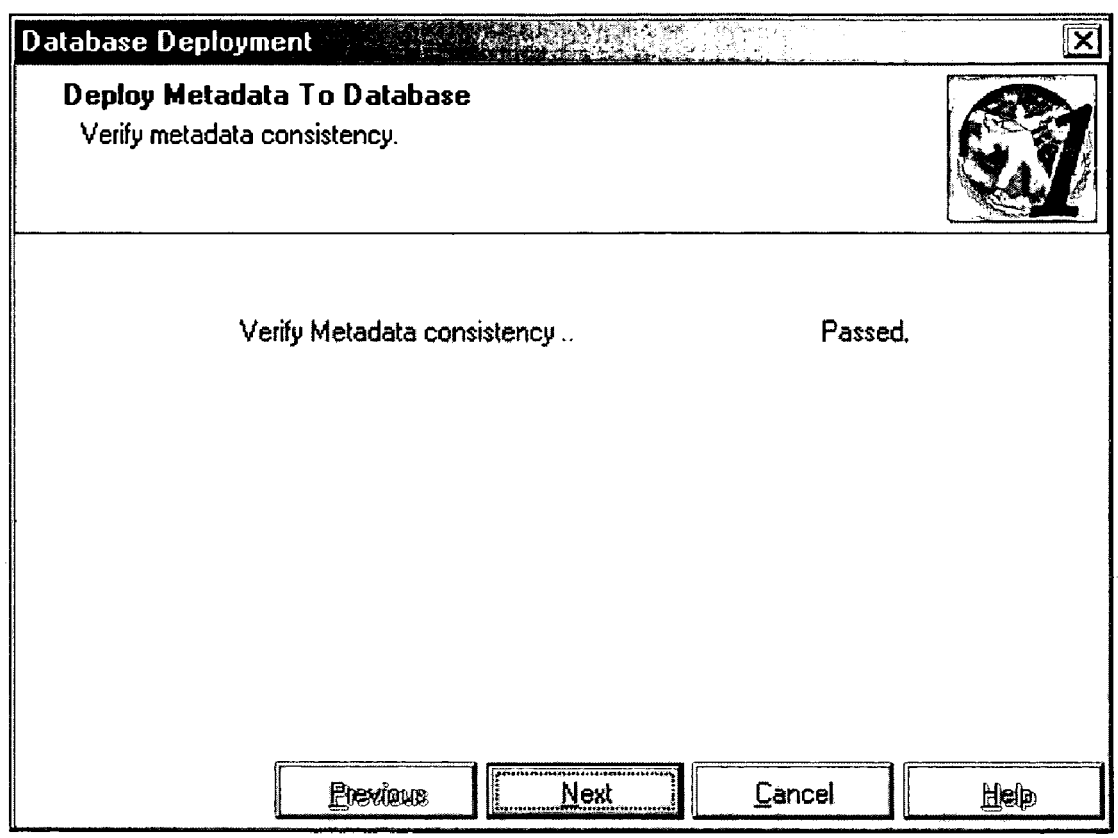
FIG. 7 is a screen indicating the successful completion of a metadata consistency check prior to metadata element deployment to the instance data infrastructure.
Figure 8:
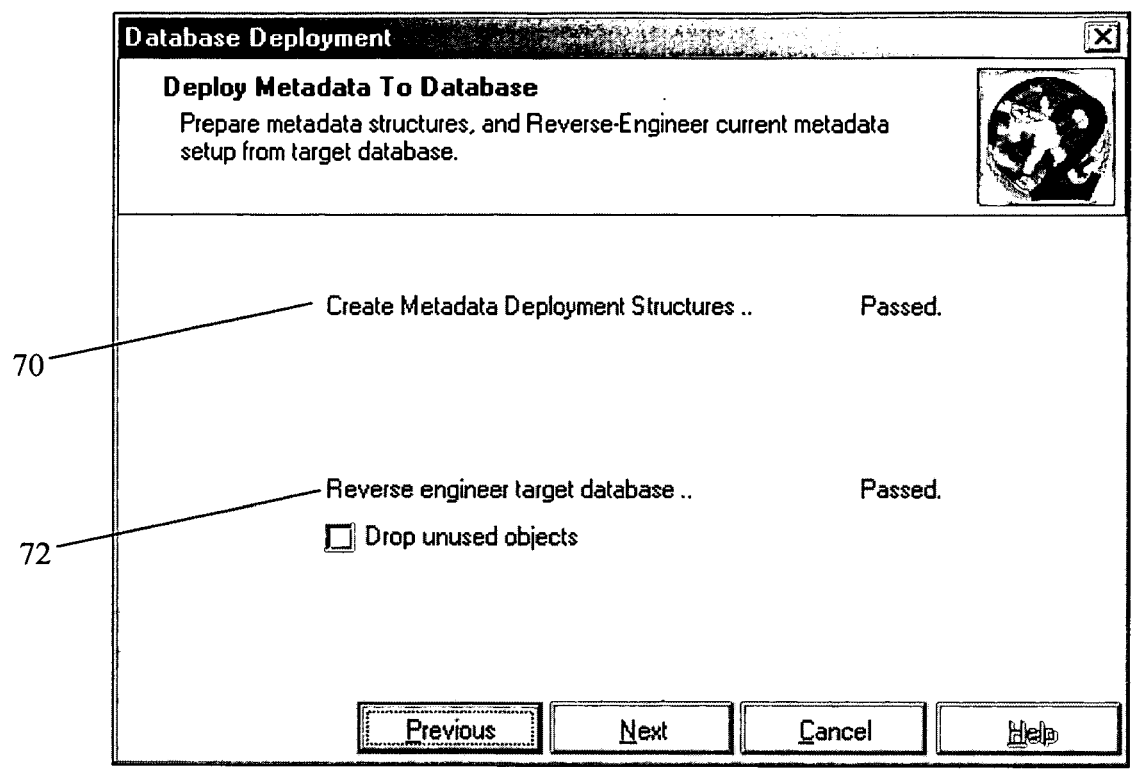
FIG. 8 is a screen indicating the completion of the comparison between the metadata elements to be deployed and pre-deployment instance data storage.

Upon deployment of a metadata element, ADM first may verify the consistency of the metadata as shown in FIG. 7. As shown in FIG. 8, ADM then may create a set of metadata structures ready for deployment 70 while also reverse engineering the back-end database 72. This allows ADM to compare what is to be deployed (along with any new changes) with the baseline of what meta data infrastructure already exists. ADM may accomplish the reverse engineering of the current back-end database through querying of the RDBMS's own cataloguing of the database infrastructure, including the database's own list of tables, table columns, constraints, indexes and triggers.

Figure 9:
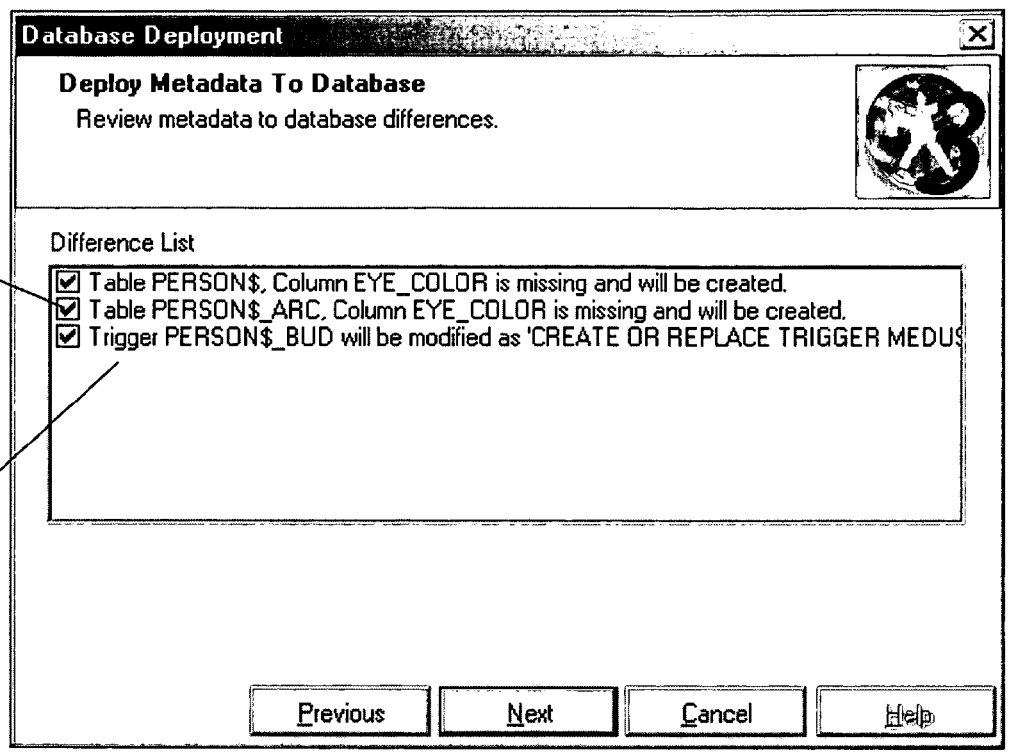
FIG. 9 is a screen is a screen indicating the changes required in order to match the instance data infrastructure to the metadata model following metadata deployment.
Figure 10:
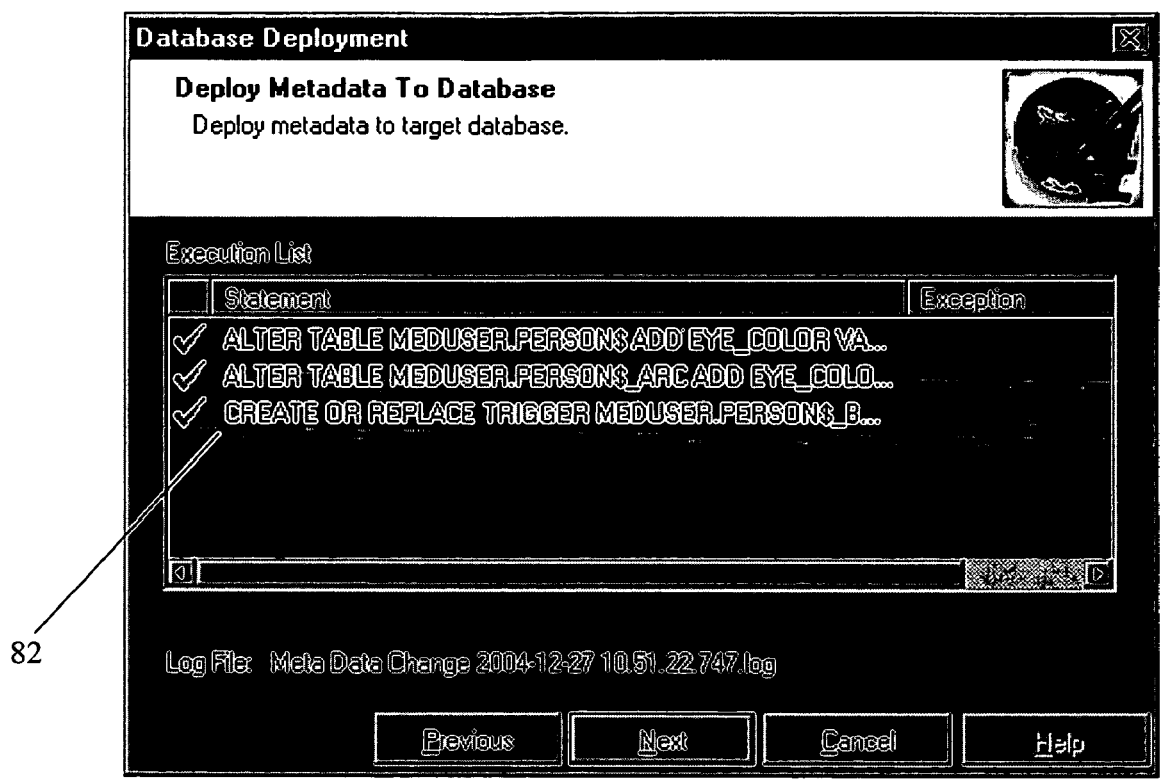
FIG. 10 is a screen is a screen indicating the successful execution of SQL statements necessary to implement the changes required to match the instance data infrastructure to the metadata model.

As shown in FIG. 9, ADM may then display the changes necessary 76 to update the back-end database with any modification (additions, deletions, or changes) to metadata elements. The administrator may be given a choice of whether or not to accept a given change using a check box 78. FIG. 10 shows the structured query language (SQL) statements 82 that may be run as a consequence of accepting changes to the back-end database. FIG. 10-B illustrates the deployment from a database perspective, whereby different metadata elements create instance data infrastructure components. The type of infrastructure component that is created depends on the data-type of the metadata element; for example a metadata element having a "container" data-type 81 that may hold other data attributes, such as a "person," may create a table 82 in the instance data infrastructure named PERSON$. On the other hand, a metadata element having a "string" data-type 83, such as a element devoted to recording last names, may create a table column 84 named "LAST_NAME" in the instance data infrastructure.

1.2—Graphs and Instance Data Storage

Figure 11:
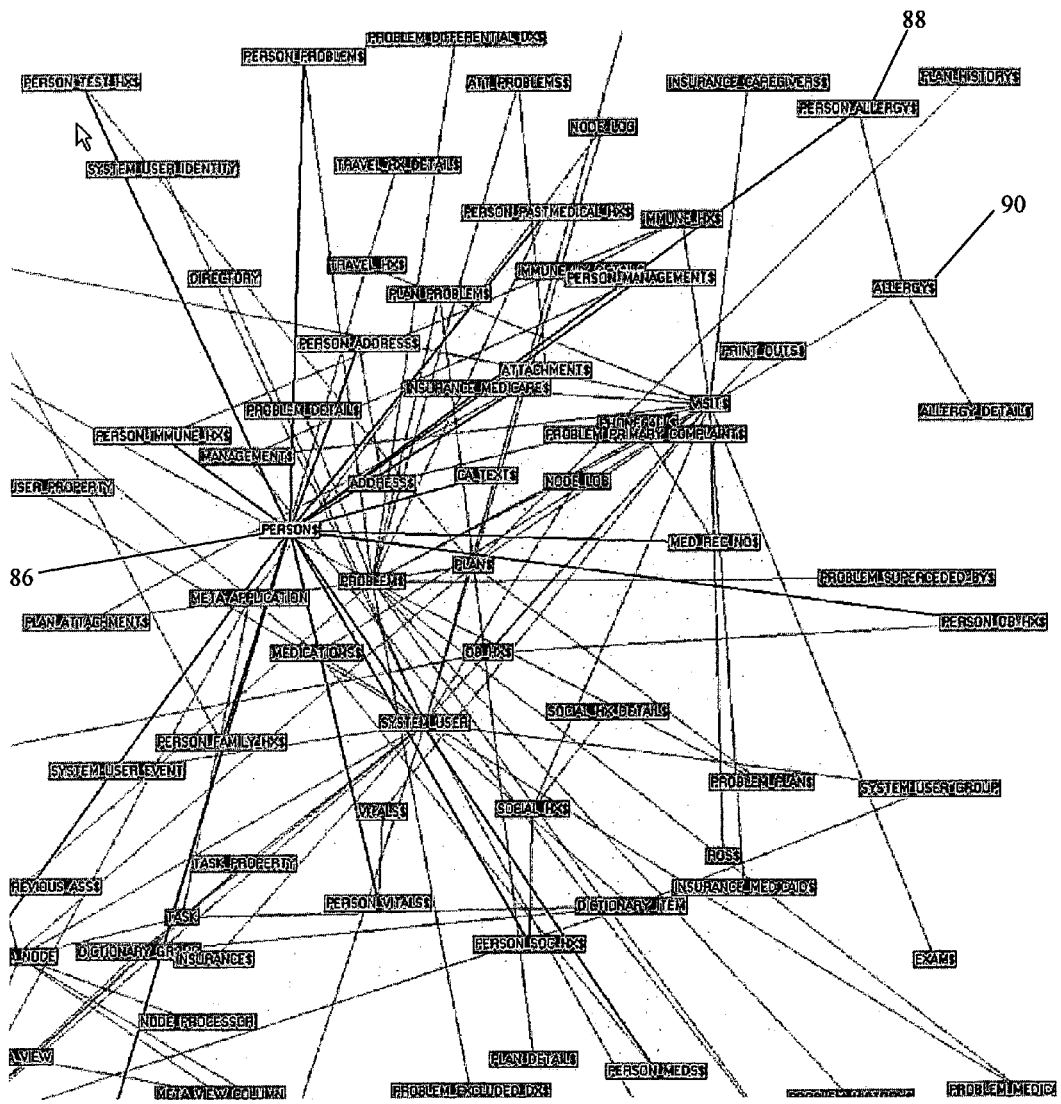
FIG. 11 is a schematic illustrating the complex interrelationships among instance data.

Recall that graph data storage may result when the data that is stored within a large databases requires complex relationships such as, for example, when tables that store data require primary-key/foreign-key relationships with more than one other table. FIG. 11 illustrates this complexity, where the hypothetical PERSON$ table 86 and its relationships to many other tables are highlighted. Some of the tables that are "children" of the PERSON$ table, such as a hypothetical PERSON_ALLERGY$ table 88, may also have another "parent"—in our example the ALLERGY$ table 90 may also be a second parent of the PERSON_ALLERGY$ table. Such multiple "parents" illustrate a graph.

Due to a graph's inherent complexity, the more a data solution is graph-like, the more likely it is to suffer from performance and efficiency problems because accessing any particular data within the graph may require accessing more data in other parts of the graph. In other words, because a graph does not present the most important information in a single location, it makes the "piecing together" of needed information laborious and time-consuming for a database server. There are very few practical solutions to graph data storage that fully address its side effects, though many important database applications require graph-like data solutions.

Different methods of storing instance data may present various solutions to the problem of graph data storage, thereby presenting different tradeoffs between efficiency from an end-user standpoint and simplicity from a development standpoint. ADM may use different methods of storing instance data, such as nodal, XML, and relational instance data storage.

Figure 12:
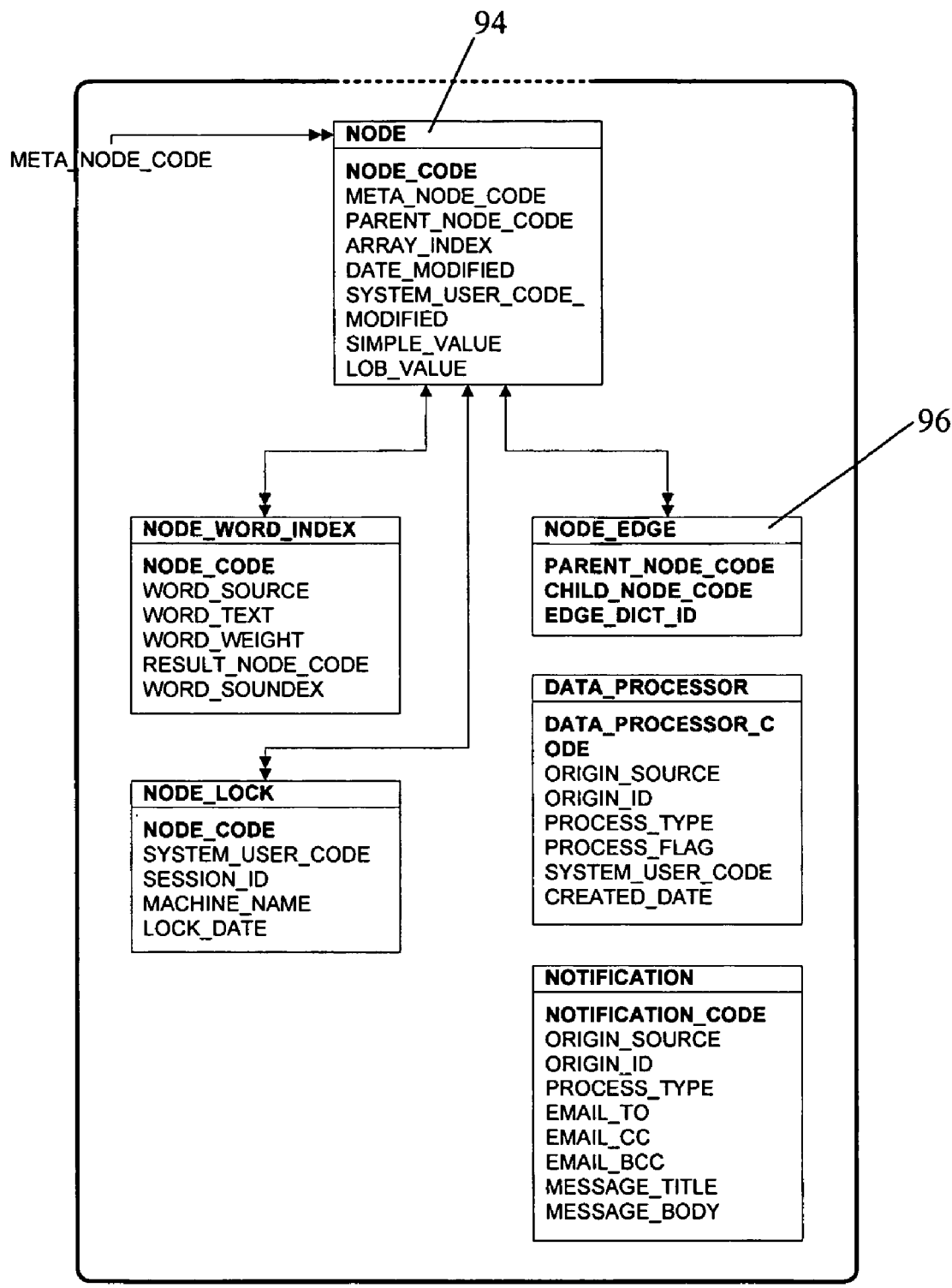
FIG. 12 is a schematic showing the nodal storage method of storing instance data and managing the relationships among instance data components.

Nodal instance storage is shown schematically in FIG. 12, and refers to the instance data being organized in a set of tables, all having one or more data relationships to two tables that may be called NODE 94 and the NODE_EDGE 96. These tables thus may manage all of the relationships between the tables housing the instance data, and also may manage the relationships between the instance data and the metadata. Nodal storage of instance data may provide a good combination of efficiency and simplicity.

XML instance data storage refers to the instance data being organized in XML documents, which are in turn housed in the relational database. Using this method, all of the data relating to a particular object, such as a person, may be stored in a single XML document. A particular type of relational database data-type, such as Oracle's character large object (CLOB) data-type, in turn may store the XML document and may make it available upon request by ADM. XML storage of instance data may provide increased efficiency and simplicity gains.

Relational instance data storage refers to the instance data being organized in a discrete set of tables, but in contrast to nodal storage, there may be no centralized table or set of tables governing the various relationships among the tables and the metadata. Instead, the relationships may be created in a decentralized fashion—various instance data tables may govern their own relationships with other instance tables, and may govern their own relationships with other tables deployed by the metadata. Relational instance data storage is shown schematically in FIG. 4, which illustrates the dynamic creation of instance data storage (also termed "$ Tables") through the deployment of metadata elements 48. Relational instance data storage trades simplicity for efficiency; it may be more complex than nodal instance data storage, but it may result in great efficiency gains because it dramatically spreads the database's table lookups among many tables rather than fewer tables, facilitating maximum use of the relational database mechanism and scalability.

Relational instance data storage thus may present the best overall solution the problem of graph data storage by confronting the growth, scalability, and efficiency issues that plague graph-like implementations. Namely, because of the complexity of accessing data stored as a graph, as instance data grows, data access may become slower. Due to the intrinsic nature of a graph, access to any part of the graph might result in accessing more parts of the graph. In other words, a graph does not present the most important information in a single location. ADM's inventive combination of using a metadata model and its management of the instance data in a table driven infrastructure—whereby the relationships and constraints among the instance data and between the metadata and instance data are managed in a decentralized fashion—overcome inefficiencies associated with graphs and ever-increasing amounts of instance data. The ability to confront the problems posed by graph solutions is in addition to ADM's ability to use simpler tree structures in an optimized data model stored in a relational database.

1.3—How ADM Interfaces with Databases and Users

ADM may provide a development environment. It may provide a simple component interface to the complex back-end data storage. This interface simplifies access to instance data. The development environment includes a component object model (COM) object, accessed from all applications referencing ADM, and an administration tool for model management. ADM has been developed for access from conventional development environments (e.g. Microsoft Visual C++ and Visual Basic, Borland Delphi) as well as web environment tools such as Microsoft Active Server Pages (ASP) or the like. ADM can create a compiled application that may be run either as a web-application or on a "fat" client (i.e., a client within a client-server architecture that performs the bulk of the data processing operations); thus it is well suited for short transactions that are characteristic of web environments.

ADM may be used with a relational database (e.g. Oracle, Microsoft SQL Server, Sybase, Informix) running on a variety of server platforms (e.g. Windows, UNIX, Linux) to provide data storage. A set of components, developed as COM objects, may allow access to the stored data to users via front-end applications. These front-end applications may be run on personal computers that operate using Microsoft Windows operating systems or the like.

The component object model, or COM, is a protocol that defines a standard way for objects that are created using object oriented programming to speak to one another, regardless of the specific way in which they actually implement methods and properties. More specifically, COM is a specification that defines how to call methods on objects.

ADM thus may access the database server via a COM object, which may be provided as a dynamic link library (DLL). This setup guarantees that no other software disrupts ADM operations. ADM's COM object assumes several roles, including a single interface to all run-time and maintenance functions of ADM and finely tuned algorithms for data access. In other words, the COM layer provides the end-user application with the most efficient access to the database. ADM's database may be designed to be self-sufficient, or may use a set of Windows Services for maintenance.

Various functions within the ADM COM object may allow for lock or concurrency management, or the management of simultaneous changes to identical instance data. For example, ADM may lock a particular set of instance data upon a user accessing it, thereby preventing a different user from modifying that set of instance data. Alternatively, ADM may allow two or more users to simultaneously access and modify (add, delete, or change) a particular set of instance data.

ADM may be complemented by VisualADM, thereby fitting to the object-oriented document-view paradigm: ADM may provide the data back end (document layer), while VisualADM may provide user interface(s) to the user (visual layer). VisualADM may be a thin-client form based application—forms may be defined as scripts, stored into ADM database, and retrieved at the VisualADM client location when requested. VisualADM also may provide a robust scripting language, allowing forms to implement any type of business rules. VisualADM thus may be the client-side component of ADM by allowing administrators and users to interact with ADM using a graphical user interface (GUI). VisualADM also may implement the ability to produce Microsoft Windows GUI-driven applications. VisualADM thus may be a thin-client form based application—forms may be defined as scripts, stored into ADM database, and retrieved at the VisualADM client location when requested. VisualADM may provide a robust scripting language, close in concept to JavaScript and the like, which may allow forms to implement any type of business-rules.

The VisualADM rule engine is the piece of software that may process all user requests to modify and create data or alter the user interfaces once a view is retrieved from ADM, parsed, and rendered as a form. The rule engine, in effect, may act as interaction glue between data layer and visual layer. As instance data is inserted or updated into the data repository, rules may fire to take actions. For example, when a hypothetical laboratory result is saved into the data repository, a laboratory predicate (i.e. a rule or set of rules specifically targeted toward one laboratory vendor, or all laboratory results) may fire to determine if the result is abnormal, to possibly create tasks, send email(s), add additional data, etc. ADM's Rule Engine may be implemented as a Windows Service, using existing ADM data queuing services, and existing VisualADM object-oriented libraries.

ADM may provide data access to any user from the relational database manager standpoint, by allowing the definition of views. A view may be a transform of many metadata elements, tightly or loosely connected. As instance data is created, any user may access the instance data represented as views, from any tool that can access a database using SQL, such as Microsoft Access or Microsoft MS Query. SQL is the standard language whereby data on a relational database is accessed and modified. Also, ADM permits presentation of stored data as conventional tables (data view) for standard reporting. As the data changes and expands, the content of the data views reflects the changes. Any of these data views may be defined by end users and created automatically by an the ADMAdministration tool. Moreover, ADM provides a transactional data access model suitable for web-based and client-server implementation.

Figure 5:
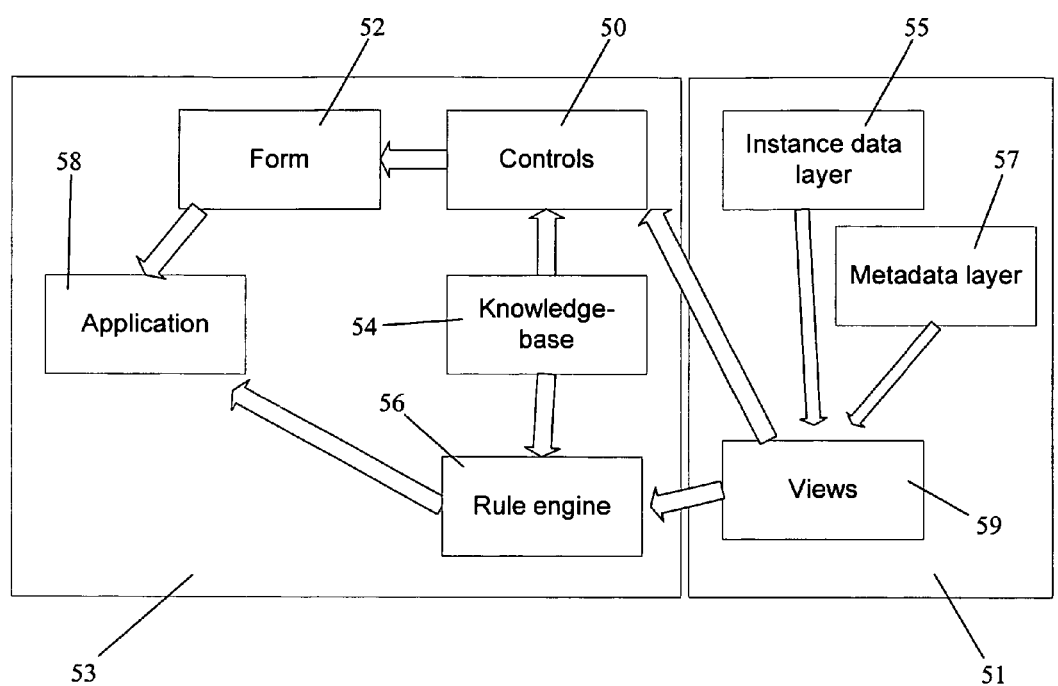
FIG. 5 is a schematic of interactions between ADM and VisualADM.

Turning to FIG. 5, the interaction between ADM's data layer 51 and the visual layer 53 provided by VisualADM is schematically shown. Metadata elements 57 and instance data 55 may be transformed into views 59, which through the use of controls 50, and then may be rendered into forms 52. Forms may comprise the end-user application 58. As described above, the rule engine 56 may perform additional checks on the data rendered by the form and may take specific actions. A separate knowledge-base module 54 may provide "substance" to the controls and rule engine by providing those components with access to pertinent information. For example, if the application ultimately is to allow the entering of "allergy" data, the knowledge-base may provide a given control or a given rule a list of allergies. The application thus may allow a user to choose the correct allergy from the list, or to add a new one, for example.

Figure 13:
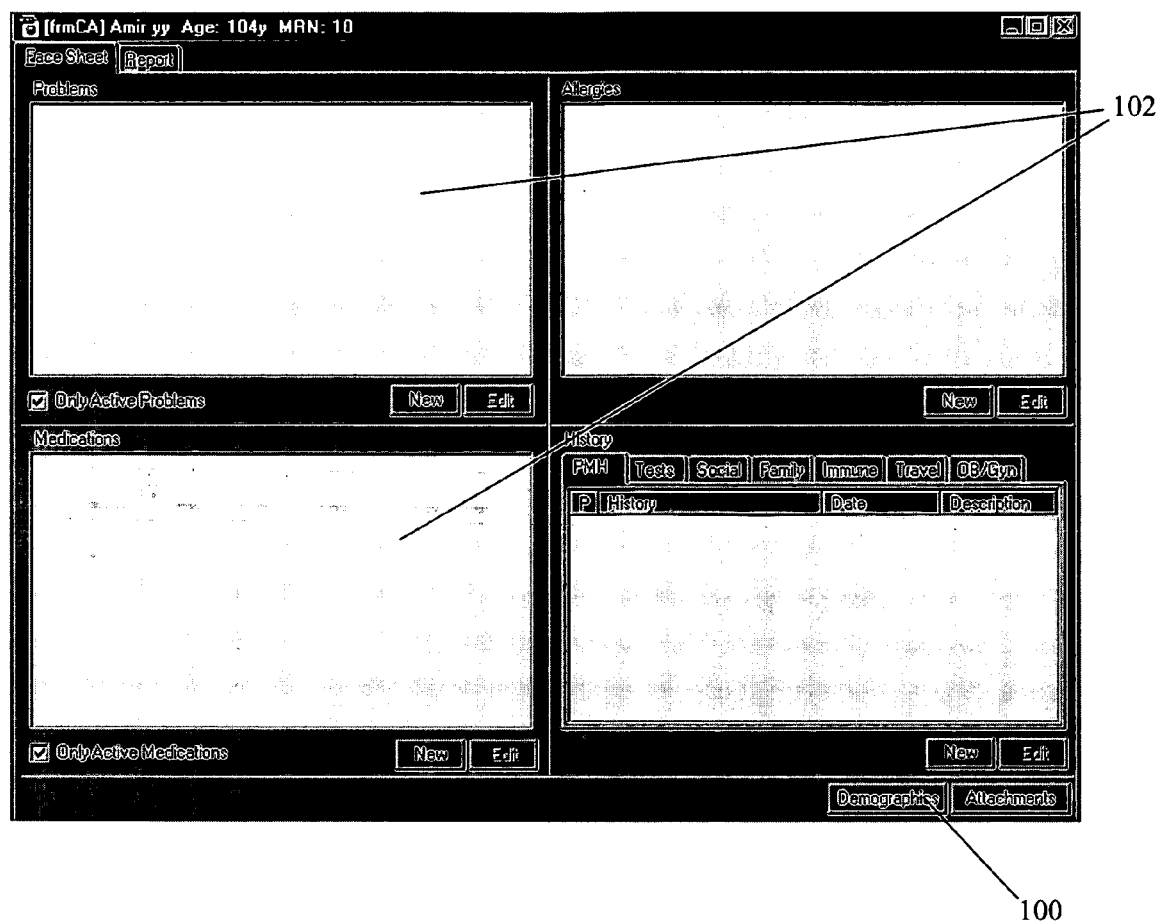
FIG. 13 is a screen generated by VisualADM whereby users may access different areas, thereby managing work flow within an enterprise.

ADM may allow the management of business or work flow within an enterprise. This is because the ease of altering the instance data storage infrastructure and the ease of developing GUI applications may allow a business to use ADM to manage appointment or scheduling data along with other substantive data attributes through a single interface. An example of such an interface is shown in FIG. 13. For example, in the medical context, a patient's scheduling information may be accessed or edited by a receptionist through a button 100 or the like made available on the form. A doctor simultaneously may access and review that patient's medical data thorough different components, such as text boxes 102, on the same interface.

Figure 14:
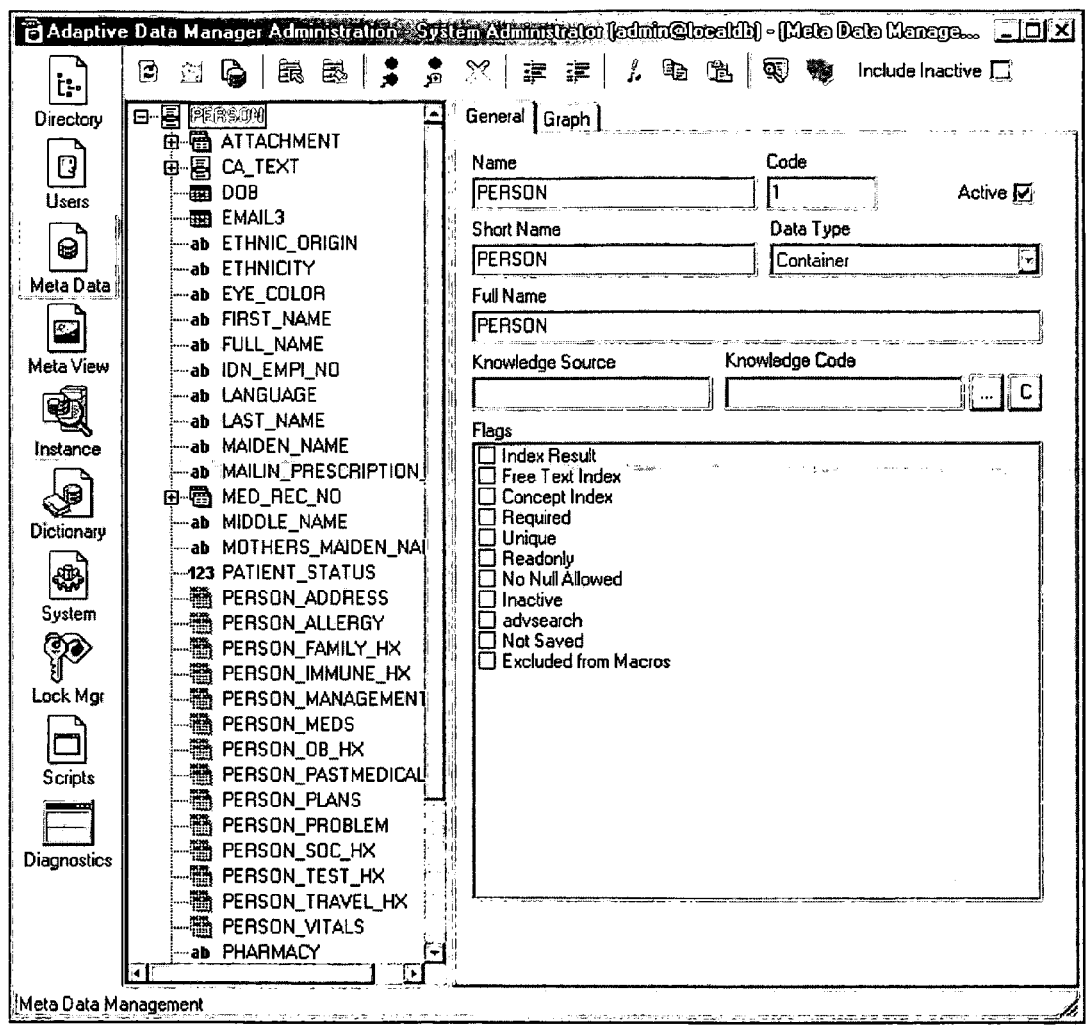
FIG. 14 is a screen of the ADM Administration Utility.

Turning to FIG. 14, ADM may be managed through an administration tool that is rendered graphically as a Windows application or the like. The administration tool may allow an authorized user to manage directories, users, metadata elements and the metadata model, views, instance data, lock and concurrency of data, scripts, dictionaries, and other ADM components.

ADM and VisualADM may be provided as a pair of InstallShield applications—ADM may be installed on a server and VisualADM may be installed on a client. The complete ADM package may consist of the ADM COM object, the administration tool and its associated documentation, a user manual, executable files, and a sample implementation. A running instance of a relational database, such as Oracle or the like, may be required prior to the installation of ADM.

1.4—How ADM Handles User Access and Security

There is a need for security to avoid unauthorized access to data. Security concerns may be especially critical in certain applications that require the storage and use of sensitive data. For example, medical record data often contains sensitive information. ADM's Security may be based on a multi-tiered role-based authorization and authentication scheme, whereby a particular user may log in to ADM using a username and password and be subjected to two different roles: one defined by ADM and another role that is native the RDBMS. ADM may store its own role definitions and user management scheme in the relational database, but this is not to be confused with the database's own user management.

For example, ADM may create two separate classes of roles for users using the relational database, such as "user" and "administrator." In addition, ADM may add its own roles such as "doctor," "nurse," and "ADM admin." The ADM roles of "doctor" and "nurse" may have different rights and privileges from each other while using ADM—a "doctor" may be able to edit a patient's the length of stay in a hospital, but a "nurse" may only be allowed to view this data. But both "doctor" and "nurse" ADM roles may be part of the "user" role at the database level. In contrast, the ADM role of "ADM admin" may be part of the "administrator" role at the database level, thereby allowing a user with this role to create other users, alter the instance data storage infrastructure, and the like.

Because ADM may subject users to both its own security and a RDBMS-assigned role, it may take advantage of special security features provided by the RDBMS vendor. Oracle, for example, provides a number of security features that may be utilized by ADM, including strong encryption, role-based access and auditing capabilities, which make its security system much more difficult to breach. Because the underlying security mechanism of the RDBMS may be used, ADM may use the database's auditing features to determine which user made a change to data (who), what change to data occurred (what), and at what date and time the change to data took place (when).

2.—COM Technical Manual

The ADM COM Object achieves mainly three distinct functions: data access and indexing, data transformation, and administration. These functions are available through several separate interfaces:

ADM.Profile

ADM.Profile is the gateway interface to ADM. An instance of the ADM.Profile interface must be created prior to any other ADM interfaces. In order to fully set the ADM.Profile interface, both successful login transaction to the Oracle database and user identification (either using trusted authentication or explicit authentication) are required. The profile interface is then communicated to any other interface for safely communicating user and database information.

☐ Note. DCOM may be used to access ADM interface services; trusted user authentication will be not be available in that mode.

ADM.Datagate

ADM.Datagate is the interface allowing data access. It provides multiple paths to access, add, modify, and delete any stored data (i.e. instance data). ADM.Datagate is also the interface for processing search requests.

ADM.Lock

Data elements accessed via the ADM.Datagate interface are read-only unless the user requests exclusive access to portions of the data: during this process, locks will be placed on data elements, guaranteeing exclusive read/write access to the data.

The ADM.Lock interface is a purely administrative interface. This interface allows the ADM Administrative Utility to monitor and delete locks.

ADM.Dictionary

Relational database model always includes dictionaries or reference tables for standard values. For example, if a study includes a field for 'Gender', the values for gender may be coded as 1 being 'Female' and 2 being 'Male'. Only '1' or '2' will be stored into the instance data, thus possibly allowing the description to be changed later without affecting the instance data.

ADM.Dictionary supports this model by providing methods to query codes and descriptions, retrieve a description given a code, etc.

ADM.Index

ADM.Index is the interface supporting document indexing under the Adaptive Data Manager paradigm. Indexing is declared at the Meta data level in the form of indexing flags, and any instance data creation will result in indexing requests. The ADM.Index interface is the open interface allowing for any external application to process requests resulting in keyword or concept indexing. This interface will be used, typically, by processes (or services) or applications monitoring newly created data and processing the request for indexing.

ADM.Metadata

The Meta data is the structure formally defining how data is collected. This interface is purely administrative: only the ADM Administrative Utility will make use of this interface. Note that inexperienced use of this interface may be detrimental to existing data elements.

☐ THIS DOCUMENT DOES NOT PROVIDE TECHNICAL DOCUMENTATION FOR THIS INTERFACE. THIS INTERFACE IS STRICTLY FOR MODEL MANAGEMENT, AND SHOULD NOT BE ACCESSED INTO A REGULAR APPLICATION DEVELOPMENT SITUATION.

ADM.Metaview

The Meta view structure is the data transformation aspect of ADM: instance data (created after the meta data defined pattern) is stored as graph into the database. Such organization does not easily enable users to report on any data elements. The Meta view structure allows users to define views as collections of meta data elements: when processed, these views are physical oracle tables, accessible by any user (with proper connection rights) with any SQL enabled tools.

The ADM.MetaView interface is purely administrative: only the ADM Administrative Utility will make use of this interface. This interface also works in conjunction with several server-side services.

☐ THIS DOCUMENT DOES NOT PROVIDE TECHNICAL DOCUMENTATION FOR THIS INTERFACE. THIS INTERFACE IS STRICTLY FOR MODEL MANAGEMENT, AND SHOULD NOT BE ACCESSED INTO A REGULAR APPLICATION DEVELOPMENT SITUATION.

ADM.Script

The ADM.Script interface is the support interface for the Visual ADM suite of tools: Visual ADM's APPLICATION BUILDER is the application managing data using ADM.Script; Visual ADM's FORM RUNNER is the application using this interface for end user processing.

Note that this interface is only accessed from Visual ADM tools.

ADM.User, ADM.Facility, ADM.Directory

These interfaces allow management of information related to user, security and user access rights.

These interfaces are purely administrative: only the ADM Administrative Utility will make use of these. Any information for a currently logged in ADM interface used is available through the required ADM.Profile interface.

☐ THIS DOCUMENT DOES NOT PROVIDE TECHNICAL DOCUMENTATION FOR THESE INTERFACES. THESE INTERFACES ARE STRICTLY FOR MODEL MANAGEMENT, AND SHOULD NOT BE ACCESSED INTO A REGULAR APPLICATION DEVELOPMENT SITUATION.

ADM.Dataaccess

TODO

☐ Note to the Reader.

The syntax between IIS' Active Server Pages (ASP) and Delphi may be different. In the case of Delphi, most function calls use square brackets after the function name, while parentheses are used after function names in ASP.

For information relating to the ADM management refer to the 'ADM Administration Utility User Manual' document.

ADM.Profile

Introduction

The Adaptive Data Manager (ADM) is a data storage solution, and as such, must enforce and guarantee safety of stored data. ADM achieves this goal with complementary approaches:

By controlling user logins and users data access rights

By keeping an audit trail of all user transactions (creations, updates and deletions) at the field level. Any user-modified data element is archived and tagged with the user information and date.

The ADM.Profile interface is the interface enforcing security with ADM. In order to access any of the interface services provided by ADM, one must successfully provide accurate information to log to the Oracle-based ADM data store, and also authenticate self as a registered ADM user.

Information required to log on to the Oracle data store consists of connection string, data store user name and password, and authentication user name and password information.

☐ The Connection string specified OLE DB provider and necessary parameter information for the provider. For correct data retrieval, Oracle Provider for OLE DB should be used.

User authentication information is either using trusted authentication or explicit authentication.

Trusted authentication: the user has already satisfied corporate security when accessing network resources, and therefore the ADM Profile interface can assume that the user is trustworthy. Network trusted authentication information is gathered by the ADM Profile interface and is checked for authentication. In other words, no input is required from the user.

Explicit authentication: A user name and password is required from the user.

☐ The ADM Profile interface may be created using DCOM; in this case, trusted authentication couldn't be used, as the running instance of the ADM component is instantiated on a remote computer host and, thus, does not represent current user credentials.

ADM.Profile Tools and Functions

Connection Procedure

IProfile is the interface granting access to any of the other ADM interfaces. Therefore, in order to access any of the ADM interfaces, one must first successfully create and connect an IProfile interface. For example, using Delphi,

```
var
    pProfile, pInterface: OLEVariant;
begin
    try
        pProfile := CreateOLEObject('ADM.Profile');
        if pProfile.Open['Provider=OraOLEDB.Oracle.1;Persist Security
Info=False;User
ID=test;Data Source=tiger', 'test', 'scott', 'host'] and
pProfile.Authenticate[1, '', ''] then
            try
                pInterface:=CreateOLEObject('ADM.xx');
                pInterface.SetProfile(pProfile);
                [...]
                pInterface:= unassigned;
            except
                [...]
            end;
            pProfile := unassigned;
    except
        [...]
    end;
end;
```

In other words, a profile is created, and a connection is established to the Oracle ADM data store; user authentication is immediately established using the Authenticate( ) function. Note that user authentication may be either explicit or trusted.

Once the profile object has been successfully initialized, this object can be communicated to other ADM interfaces as a short hand for communicating database and user profiling. Note that a profile interface must be fully defined (both connected to a data store and user authenticated) in order to be communicated to another interface (using the SetProfile( ) function).

Reviewing and Verifying Access Rights

The IProfile interface describes security attributes to all other ADM interfaces using the HasPermission( ) function. The HasPermission( ) function returns a permission value for some object within a class of object interface. The iDirectoryType value defines the interface; possible interfaces are Facility, User Group, User, Meta Data, Meta View, Script and Dictionary interfaces. The Permission Type value is defined by interface: this value must be supplied in the context of the interface, and must be legal by interface. Using the ViewProfile( ) function is very similar to the HasPermission( ), only differing to that this function returns all rights for a specific interface instance element.

Database Connection and Transactions

The IProfile interface performs database transactions for all other ADM interfaces using the Execute( ) function. A SQL statement is passed as a parameter to the Execute( ) function, and if the transaction is successful, Execute( ) returns a record set from which individual field values are retrieved.

Function Reference
Open
Description Function

Establishes a connection to an Oracle database. This connection must point to an IMO's Adaptive database model.

Returns TRUE if connection is established, FALSE otherwise. If connection was not established, check content of LastError to get a description of the connection failure. Note: strConnection string specified OLE DB provider and necessary parameter information for the provider. For correct data retrieval, Oracle Provider for OLE DB should be used.

Syntax Function Open(const strConnection, strUserName, strPassword, strHost: String): boolean Authenticate
Description Function Authenticate the user, either using explicit or trusted authentication. Set the first parameter of Authenticate( ) to 0, and provide a user name and password to proceed to explicit authentication. Set the first parameter of Authenticate( ) to 1 to proceed to trusted authentication. In this case, note that no values are necessary for username and password parameters.

Returns TRUE if user authentication succeeded.

Syntax Function Authenticate(const iAuthentication: longint; sUsername, sPassword: String): boolean HasPermission
Description Function The HasPermission( ) function returns a permission value for some object within a class of object interface. The iDirectoryType value defines the interface; possible interfaces are Facility, User Group, User, Meta Data, Meta View, Script and Dictionary interfaces. The PermissionType permission value is defined by interface: this value must be supplied in the context of the interface, and must be legal by interface.

Possible numeric values for iDirectoryType are:
0 Undefined
1 Facility
2 User Group
3 User
4 Meta Data
5 Meta View
6 Script Possible numeric values for PermissionType, by interface are:

| Interface | Value | Description |
|---|---|---|
| Facility | 0 | Create |
| | 1 | Read |
| | 2 | Update |
| | 3 | Delete |
| User Group | 0 | Create |
| | 1 | Read |
| | 2 | Update |
| | 3 | Delete |

-continued

| Interface | Value | Description |
|---|---|---|
| User | 0 | Create |
| | 1 | Read |
| | 2 | Update |
| | 3 | Delete |
| Meta Data | 0 | Create |
| | 1 | Read |
| | 2 | Update |
| | 3 | Delete |
| Meta View | 0 | Create |
| | 1 | Read |
| | 2 | Update |
| | 3 | Delete |
| Script | 0 | Create |
| | 1 | Read |
| | 2 | Update |
| | 3 | Delete | sCode is the object database code corresponding to the interface identified by the iDirectoryType value. For example, if iDirectoryType is 'Meta Data', then sCode will be a Meta Node Code.

Syntax Function HasPermission(iDirectoryType: longint, sCode: String, PermissionType: longint): OLEVariant;

ViewProfile
Description Function

The ViewProfile( ) function returns all permission values for some object within a class of object interface. The iDirectoryType value defines the interface; possible interfaces are Facility, User Group, User, Meta Data, Meta View and Script interfaces. The permission value is defined by interface: this result must be interpreted in the context of the interface.

Possible numeric values for iDirectoryType are:
0 Undefined
1 Facility
2 User Group
3 User
4 Meta Data
5 Meta View
6 Script sCode is the object database code corresponding to the interface identified by the iDirectoryType value. For example, if iDirectoryType is 'Meta Data', then sCode will be a Meta Node Code.

Syntax function ViewProfile(iType longint, sCode: String): OLEVariant;

Properties
Description Function

The Properties property returns properties related to the user identified as part of the Authentcate( ) method call.

Possible values for Item are:
NAME Returns the user full name
LASTNAME Returns the user last name
FIRSTNAME Returns the user first name
CODE Returns the user code
LEVEL Returns the user administrative level
USERNAME Returns the user username
ROLES Returns the user roles
ACTIVE Returns TRUE if the user is active
EXTERNALID Returns an additional administrative ID for the user SESSIONID Returns Session ID
PLATFORM Returns OS platform
MACHINE Returns the computer name where ADM dll resides
DBUSERNAME Returns database user name
DBSERVER Returns database server name DBCONNECTION Returns database connection string
METADATACACHEReturns TRUE if Meta Data is cached
Syntax Property Properties[Item: String]: OLEVariant;
Connected
Description Function
 The Connected property indicates whether IProfile interface is connected to a database.
Syntax Property Connected: boolean;
Connection
Description Function
 The Connection property returns an ADO Connection object. This object is defined in the Microsoft ActiveX Data Objects 2.0 Library (see msado20.tlb) and is responsible for all database transactions.
Syntax Property Connection: _Connection;
Close
Description Function
 The Close function closes the connection to the database.
Syntax Procedure Close;
Execute
Description Function
 The Execute function executes the specified query (SQL statement) and returns resulting RecordSet.
Syntax Property Execute(strSQL: string): _RecordSet;
Sequence
Description Function
 The Sequence function returns the next unique number in the specified sequence
Syntax Property Sequence(strSeed: String): integer;
BeginTransaction
Description Function
 The BeginTransaction function begins a new database transaction.
Syntax Procedure BeginTransaction;
Commit
Description Function
 The Commit function saves any changes and ends the current transaction
Syntax Procedure Commit;
Rollback
Description Function
 The Rollback function cancels any changes made during the current transaction and ends the transaction.
Syntax Procedure Rollback;
LastError
Description Function
 The LastError function returns a concatenated string of any accumulated errors and, then, clears the error accumulator.
Syntax Property LastError;
SetDirectory
Description Function
 The SetDirectory function sets a connection between the Directory object and current IProfile instance.
Syntax Procedure SetDirectory(Directory: IDirectory);
ServerDateTime
Description Function
 The ServerDateTime function returns current date.
Syntax Property ServerDateTime;

ADM.Datagate

Introduction
 The ADM.Datagate COM object interface is a component interface that allows easy access to complex data stored on a relational database server, using the IMO Adaptive Database Manager. ADM.Datagate tremendously simplifies data modeling, design and access to very large amounts of data. The data model can be expanded or reduced at any time. Expanding the data will not affect current applications accessing ADM.Datagate interface services.
 The data that is stored through ADM.Datagate is modeled after either trees or graphs. Any real life data can be stored using either of these formal data models into ADM.Datagate. The definition of the data to be captured is defined by the Meta data, and represents the data element hierarchy and associated attributes. The user data, accessed from or sent to the ADM.Datagate COM object, is stored into the database repository as instance data. The instance data is modeled after the Meta data.

Data Store Model

Introduction
 The database methodology used by the system is a free-form data model (meta data model) that stores all collected (or instance) data in the database as granular information: Many "records" are used to represent a traditional patient demographic record, or an encounter record. For example, the visit date would be granular information about an encounter (encounter class information type) and represents an attribute of the encounter.
 This model is adaptive to any particular situation; during implementation at a specific location, many more attributes for the "encounter class", for example, can be defined without having to modify the structural definition of the database.
 These structural definitions, or meta data, are organized in the database back-end as a tree: all granular information is stored as nodes, with pointers or edges to define the parent relationships. All user data, or instance data, are themselves patterned after meta data: meta data is the framework for creating new instance data. Therefore, this design schema is data driven, allowing for rapid and dynamic customization of the system for any new data elements that present themselves.
 Complementing this design schema is a number of additional tables that store data in a traditional relational format. Security tables allow very specialized access to the system and the data stored therein. A set of archive tables provides a thorough permanent data-auditing trail.

Meta Data and Instance Data Tables
 As stated earlier, all user data within the system can be represented as a tree. The tables that make up the Meta data section of the database represent how this tree is to be stored. Take the following, for example:
 The boxes indicate the root meta nodes defined for this example, and the other elements represent the leaf meta nodes. The single database table used to define this tree is:

META_NODE
 The Meta_Node table will store all of the data definitions and their relationships for the Abstractor+database. To continue the previous example, a possible iteration (or multiple instances) of the above meta data could be represented as the following:
 Note that the meta model may have many meta roots; It is possible to define many concurrent meta model trees, and to also have corresponding separate instance data trees in the same database.
 The previous example meta model tree, instance data would be represented in the database by the following tables:

Node
 The node table encapsulates all of the current data values that were gathered in the system with the relationships between these data elements as defined by the meta data. All data stored in this node table is also marked with an owner. Modifying a row in this table will mark the new data with a new owner and save the previous data value into an archive table. The client software application provides users the ability to review all instance data versions. Deletion of any instance data in the database is strictly prohibited.

Meta View

Functionality is provided to hide the granularity of the free-form flexible database model of ADM and to enable simple access to the data enclosed into ADM. Any user, with appropriate database rights, can query the ADM data store model database using conventional tools such as Microsoft Access or Microsoft Query.

A mechanism has been created to allow users to define Meta Views constituted of meta data elements. These Meta views are created and maintained by ADM. Any change to the instance data is automatically retrofit into the Meta view structure.

Refer to the 'ADM Administration Utility User Manual' document for more information.

Identifiers

In order to simplify access to the data, any data transaction is effective using identifiers. An identifier is a string that represents any distinct data element.

Introduction

Data access is possible using identifiers. An identifier specifies where to access data. For example, let's define a hypothetical Meta data model:
Patient
Last_Name Child of Patient element
First_Name Child of Patient element
Visits[] Child of Patient element
Visit_Date Child of Visits Array element
Etc.

Each patient created into this model will be treated as a Patient element. Each Patient element will have a Last_Name, a First_Name and many patient Visits. Patient is the root for all patient related elements.

☐ Note: This example assumes that all data follows this model, while this is not totally true. We have assumed in this example that the Meta model can only have one root element, describing a patient in this example. In actuality, ADM.Datagate accepts many Meta Data element roots, for example one describing the patient, another one describing the patient provider, and one describing patient education, etc.

One instance of the Datagate object only refers to one instance data root at the same time, PATIENT begins the one in our example. Accessing the patient's last name can be done by specifying patient.last_name. The Visit element is an array of elements. Accessing the date of the first visit would be patient.visit[0].visit_date.

Identifier Reference

An identifier is a reference to a specific meta data layer element. An identifier consists of one or many identifier terms separated by a period ('.'). Each identifier term in turn is a leaf element of the instance data tree or the root for a specific branch of the instance data tree. For example,
patient.last_name
Patient is the top root of the tree, and Last_Name is a child element inside the meta data tree of elements.
patient.visit[c].admit_date
PATIENT is the top root of the tree, Visit[] is an array element where the c index indicates the current branch, and Visit_Date is a leaf element.
patient.med_rec_no[c].visit[c].diagnosis[0].code Patient is the top root of the tree, Visit[] and Diagnosis[] are array elements when the c index indicates the current branch index, Diagnosis[0] is branch 0 of the Diagnosis element array, and code is a leaf element.

Identifier abbreviations can be used, as Datagate will interpret these abbreviations at run time. Using the previous examples, the identifiers can be rewritten as:
patient.last_name
visit[c].admit_date or even admit_date
diagnosis[0].code Identifier items can be of leaf type (thus string, integer, boolean, date, real, etc.) or array type. When referring to array identifier items, one must also specify the array argument. Array arguments are of several types:

'c': The current record of the array. If the array is Visit[], then Visit[c] is the current visit. Note that the index of an array can be accessed and set using the indexOf( ) function. The c record index can be offset with an integer value. For example,
visit[c].visit_date
diagnosis[c+1].code 'n': The last record of an array. If this array is empty then an empty value will be returned. The n record index can be offset with an integer value as well. For example,
visit[n].admit_date an integer: All array records can be retrieved individually by an integer. If an array record is requested and that record has not yet been defined, then it will be created, as well as any intermediary records to make up that record index. For example,
visit_dx[0].visit_dx_medcode Datatypes Every meta data element has a data type, which specifies a storage format, constraints, and valid range of values. A variety of predefined data types are provided. A scalar type has no internal components. An array type has internal components that can be manipulated individually. The following figure shows the predefined data types.
Type Storage Family Data type
Scalar Number Integer
Real
Character String
LongString
Boolean Boolean
Date & Time Date
Binary large object Blob
Array Array Array
Virtual Array Number Types Number types allow you to store numeric data (integers and floating-point numbers), represent quantities, and perform calculations.
INTEGER The INTEGER data type is used to store signed integers. Its magnitude range is—2147483647 .. 2147483647.
FLOAT The FLOAT data type is used to store fixed or floating-point numbers of virtually any size. Its magnitude range $5.0 \times 10^{-324} .. 1.7 \times 10^{308}$. The maximum precision of a FLOAT value is roughly equivalent to 15 decimal digits.

Character Types

Character types allow you to store alphanumeric data, represent words and text, and manipulate character strings.

STRING

The STRING data type is used to store character data. The maximum amount of data that can be stored into a STRING data type is 255 characters.

LONG STRING

The LONG STRING data type is used to store (nearly) unlimited-size character data. The maximum amount of data that can be stored into a LONG STRING data type is 4294967294 characters.

Boolean Types

The following types allow you to store and manipulate logical (true, false) values and date/time.

BOOLEAN

The BOOLEAN data type is used to store the logical values TRUE and FALSE. Only logic operations are allowed on BOOLEAN variables.

☐ Note: All data types do resolve to a BOOLEAN data type. A STRING is evaluated to TRUE if not empty, otherwise FALSE. INTEGER and FLOAT are evaluated to TRUE if not 0, otherwise FALSE. A DATE is evaluated to TRUE if not Jan. 1, 1900, otherwise FALSE.

DATE

The DATE data type is used to store fixed-length date/time values. DATE values also include the time of day. The integral part of a DATE value is the number of days that have passed since Dec. 30, 1899. The fractional part of a DATE value is the fraction of a 24-hour day that has elapsed.

☐ Note: The DATE function SYSDATE returns the current date and time.

Binary Objects

Binary objects can be stored using the BLOB (Binary Large Object) data type.

Array Type

The Array data type is the data type allowing for building lists of values. Values can be a single scalar data type, multiple scalar data types thus making a record of scalar and array data types. This is the essential building block for complex business model data storage.

The virtual array data type is the data type allowing to build arrays of references of elements belonging to other arrays. For example:

Patient.Visit[].Medication[]: Medication[] is a an array of medications for the patient for each visit.

Patient.All_Medications[]: All_Medications[] could be set as a virtual array of all patient medications, regardless of the visits. Virtual Arrays are especially designed for creating summary lists, as a collection of only some array elements of another array Meta data node.

Type to Meta Data Coding

Data types are coded and accessed as numbers inside the Meta model. The following table provides the mapping between formal data types and data type number values.

Data type Number

Undefined 0

String 1

Integer 2

Float 3

Date 4

Long String 5

Boolean 6

Array 7

Array Record 8

Virtual Array 9

ADM.Datagate Tools and Functions

ADM.Datagate provides a set of functions for accessing and navigating inside atomic data as well as accessing data as a whole. Note that most functions will return data as variants, so that application data typing may be less of an issue.

Accessing Datagate

IDatagate is a COM object interface. IDatagate relies on a previously declared IProfile interface to establish a connection to the datastore. For example, using Delphi,

```
var
    pDoc, pProfile: OLEVariant;
begin
    try
        pProfile := CreateOLEObjects('ADM.Profile');
        if pProfile.Open['Provider=OraOLEDB.Oracle.1;Persist Security
            Info=False;User
ID=test;Data Source=tiger', 'test', 'scott', 'host'] and
        pProfile.Authenticate[1, '', ''] then
        try
            pDoc := CreateOLEObject('ADM.DATAGATE');
            pDoc.SetProfile(pProfile)
            [...]
            pDoc := unassigned;
        except
            [...]
        end;
        pProfile := unassigned;
    except
        [...]
    end;
end;
```

☐ Note: For more information about accessing COM interfaces refer to Appendix A, COM Interface Calling Reference.

☐ Connecting Datagate to the data store is only granted if a successful connection of IProfile was previously established. Refer to the ADM.Profile section for more information.

Managing Instance Data

Data elements are retrieved from the database by using the Open( ) function. Closing access to the data elements is set by using the Close( ) function. Saving data element changes is achieved by using the Save( ) function.

☐ Note that all data elements are read-only after calling the Open( ) function. Use SetLock( ) and CloseLock( ) functions to obtain and release read/write to the data elements.

☐ Using the Close( ) function after opening and locking data will not save the data, and will not undo the locks. Use the Save( ) function to save the data. Note that the Save( ) function will not remove the locks: use the CloseLock( ) function to release locks.

For example using Delphi:

```
[...]
b := pDoc.Open[iNodeCode];
[...]
pDoc.Close;
[...]
```

In this example, the Boolean variable b indicates if loading the pDoc Datagate object with the iNodeCode root code was successful. Note that iNodeCode indicates an instance data root node code.

Accessing and Setting Element Values

Value, Setlock, Closelock, Isreadonly

Data elements are accessed and set using identifiers through the value( ) function. For example,

```
Using Delphi:
Var a: olevariant;
[...]
A := pDoc.Value['patient.first_name'];
pDoc.Value['patient.first_name'] := 'Doe';
Using Active Server Pages:
Dim A
A = pDoc.Value("patient.first_name")
pDoc.Value("patient.first_name") = 'Doe'
```

A data element can only be set if it is in Read/Write mode. Use the SetLock( ) function to be able to write to data elements. The SetLock( ) function will return TRUE if the element was effectively locked. To check if a data element is Read Only, use the IsReadOnly( ) function.

Indexof, Count, Currentindex, Order

Access through the data element is made using identifiers. To set the current data array element, use the IndexOf( ) function. To know the size extent of an array identifier, use the Count( ) function. Note that the count function will return 1 for a non-array identifier.

For example,
Using Delphi:
pDoc.IndexOf['patient.visit[0].DX[]']:=1;
Using Active Server Pages:
pDoc.IndexOf("patient.visit[0].DX[]")=1

Note that the IndexOf( ) function only changes the DX[] array subscript for the Visit[0] array record. In other words, the DX[] Subscript for visit[1], for example, would not be affected.

After setting the current array subscript using the Index Of( ) function, it is possible to use a syntax referring to the current subscript. For example:
Using Delphi:
pDoc.IndexOf['patient.visit[0].DX[]']:=1
pDoc.Value['patient.visit[0].DX[c]']:='Heart Failure';
Using Active Server Pages:
pDoc.IndexOf("patient.visit[0].DX[]")=1
pDoc.Value("patient.visit[0].DX[c]")='Heart Failure'

DX[c] is actually making reference to DX[1]. It is possible to set all the current subscripts at once using the CurrentIndex function. For example,
Using Delphi:
pDoc.CurrentIndex :='patient.visit[2].DX[5]';
Using Active Server Pages:
pDoc.CurrentIndex="patient.visit[2].DX[5]"

In other words, the current index for User.Visit[] is 2, and the current index for User.Visit[2].DX[] is 5.

It is possible to change the order of subscripts within an array, using the Order( ) function. For example, one could set that patient visit 2 should come after patient visit 5 by writing:
Using Delphi:
pDoc.Order['patient.visit[2]']:=5;
Using Active Server Pages:
pDoc.Order("patient.visit[2]")=5

Delete

The Delete( ) function allows for element management, by allowing deletion of any element. Note that the parent of the element being deleted must be locked, i.e. into a read-write state. Refer to the SetLock( ) function for more information.

Creating and Adding New Element Values

Value

A whole new tree can be made by creating a new instance of the ADM.DATAGATE object, establishing a connection, and starting to assign values to the new instance pointer using the Value[] property. For example, Using Delphi:

```
Var
    pDoc, pProfile: OLEVariant;
[...]
    pDoc := CreateOLEObject('ADM.DATAGATE');
    if pDoc.SetProfile(pProfile) then
        [...]
        pDoc.Value['user.last_name'] := 'Doe';
        [...]
        pDoc.Save;
[...]
Using Active Server Pages:
dim pDoc
dim pProfile
    [...]
        pDoc = CreateOLEObject("ADM.DATAGATE")
        if pDoc.SetProfile(pProfile) then
            [...]
            pDoc.Value("user.last_name") = "Doe"
            [...]
            pDoc.Save
[...]
```

Add

New elements are created using the Value[ ] property and the Add( ) function. A new array record is created using the Add( ) function. This presuppose that the array is in read/write mode, i.e. a call to SetLock( ) was previously made. For example, Using Delphi:

```
Var L: longint;
[...]
L := pDoc.Add['user.visits[ ]'];
Using Active Server Pages:
Dim L
L = pDoc.Add("user.visits[ ]")
```

The returned value, L, is the subscript for the new array record. Note that the identifier must be an array, and thus, must have the '[]' notation.

Set Operations

XML

Data elements can be accessed or set, either in parts or in entirety, using the XML property.

Searching the Adaptive Meta Manager

Find, Findkeyword, Properties, Nodeinformation

ADM.Datagate instance data can be queried using the Find, FindKeyword, Children and NodeInformation functions. Find( ) or FindKeyword( ) are the functions initiating the query, FindFirst( ) returns the first result and FindNext( ) returns all subsequent results. FindFirst( ) may be called again to loop through the result set without calling Find( ) or FindKeyword( ) again. Refer to following respective sections for Children, NodeInformation, FindFirst and FindNext functions.

Find

The Find( ) function allows for simple element queries, such as 'user last name is Doe and user first name is John'. This function allows for any combination of Boolean operators and parentheses to support such queries. The syntax for the Find( ) search argument is as follows:

statement->bexpr
bexpr->bterm {'or' bterm}
bterm->bfactor {'and' bfactor}
bfactor->'('bexpr')'|MetaID relop factor['using''soundex']
 |MetaID|'START' 'WITH' number
relop->'<'|'<='|'<>'|'>'|'>='|'='|'like'|'is null'|'is not null'
factor ->number|String|MetaID In other words, one can search for all instance data trees that have a Last_Name defined:
Find['LAST_NAME']
.. or find all records where the last name is "Doe":
Find['LAST_NAME="DOE"']
.. or find all records with a last name where the first name is "John":
Find['LAST_NAME and FIRST_NAME="JOHN"']

☐ Note that the search argument is not case sensitive.
☐ Note that string search arguments are enclosed in double quotes (" ").
☐ Note that the meta data element is not a long name such as person.last_name, etc. it is only the specific meta element, such as in this example 'last_name'.

A more complete example could be as such:
Using Delphi:

```
. . . // pDoc is an olevariant, has been previously created, and has been
assigned a profile object.
    [. . .]
    if pDoc.Find['LAST_NAME = "DOE" AND
    FIRST_NAME="JOHN"'] > 0 then
    begin
        if pDoc.FindFirst[i] then
        repeat
            // the value of 'i' is the top root node satisfying the
            query
        until not pDoc.FindNext[i];
    end;
Using Active Server Pages:
. . . // pDoc is an olevariant, has been previously created, and has been
assigned a profile object.
. . .[. . .]
    if (pDoc.Find("LAST_NAME = ""DOE"" AND
    FIRST_NAME=""JOHN"" ") > 0) and
    (pDoc.FindFirst(i)) then
    do
        // the value of 'i' is the top root node satisfying the
        query
        [. . .]
    loop until not pDoc.FindNext(i)
    end if
```

These examples show a query initiated using the Find( ) method. The Find( ) function returns the number of elements matching the criteria set. The first element is retrieved using the FindFirst( ) method. Note that FindFirst( ) returns a Boolean value to indicate if the call to FindFirst( ) was successful. After making use of this value, FindNext( ) is called to retrieve the next element. Note again that FindNext( ) returns a Boolean value to indicate if the call to FindNext ( ) was successful. FindNext( ) will return FALSE when the last entry has been retrieved using FindNext( ).

☐ Only data saved into the data store will be queried using this method. In order to have the data stored in memory also queried, save the data first before performing a query.

'Start with' Expression

It is sometimes necessary to perform queries within a range of elements, such as the current data gate element, for example. Such element usually identifies the top of the tree (or sub-graph) where search results are meaningful. This can be achieved using the 'START WITH' expression, and specifying a node code being the top of the local sub-tree or sub-graph.

FindKeyword

The FindKeyword( ) function allows for keyword or concept searches for a specified portion of the data store or for the whole data store. For example, if the Adaptive Data Manager data store has data elements about users and media articles, then one could look for all articles making references to 'Chest' and 'Pain', within the 'Media[]'branch. Note that the search is case insensitive. FindFirst( ) returns the first result and FindNext( ) returns all subsequent results. FindFirst( ) may be called again to loop through the result set without calling FindKeyword( ) again.

Several options are available to broaden or qualify the search. Refer to the Options[] property for more information.

The FindKeyword( ) can be provided with a portion of the data element tree as a starting point and will return all matching elements within that portion of the tree, or can be provided with no specific starting point and thus will query the whole data store.

Specifying a portion of the data store tree is similar to searching across all xxx, of the tree must have been fetched using the open( ) function prior to executing a search using the FindKeyword( ) function A relevant example could be:

Using Delphi:

```
Var
    b: boolean;
    i: olevariant;
[. . .]
if pDoc.Open([. . .]) then
    [. . .]
    if pDoc.FindKeyword['Media[ ]', 'CHEST PAIN'] > 0 then
    begin
        pDoc.FindFirst[i];
        repeat
            // the value of 'i' is the top root node satisfying the query
        until not pDoc.FindNext[i];
    end;
```

Using Active Server Pages:

```
Dim pDoc, i
[. . .]
if pDoc.Open([. . .]) then
[. . .]
    if (pDoc.FindKeyword("Media[]", "CHEST PAIN") > 0) and _
        (pDoc.FindFirst(i)) then
    do
        // the value of 'i' is the top root node satisfying the query
        [. . .]
    loop until not pDoc.FindNext(i)
end if
```

In both examples, an instance of ADM.Datagate (pDoc) is created and receives a connection to the data store. The pDoc instance is then loaded (open( )) to receive Media[] information, and the FindKeyword( ) function is executed to find all media articles that have the words chest and pain as keywords or concepts. Note that FindKeyword( ) returns the number of elements matching the criteria set. The first element is retrieved using the FindFirst( ) method. Note that FindFirst( ) returns a Boolean value to indicate if the call to FindFirst( ) was successful. After making use of this value, FindNext( ) is called to retrieve the next element. Note again that Find Next( ) returns a Boolean value to indicate if the call to FindNext ( ) was successful. FindNext( ) will return FALSE when the last entry has been retrieved using FindNext( ).

☐ Note that only data saved and indexed into the data store will be queried using this method. In order to have the data stored in memory also queried, save the data first before performing a query.

☐ In the case of performing searches with no specific start portion of the data store, one has to query and/or verify the data type of elements that are returned. Refer to the IsA( ) function for more information about type casting and type checking.

Properties

Properties[] property is used to refine the instance data results. Results from the FindKeyword( ) function can be tuned to return a range of results using Properties[] with FUZZY option. For example, a search can also include close enough terms using the FUZZY option. All entries similar through Soundex algorithm to the original entry will be returned as well. The Properties[] property is set or accessed as a string.

For example, using Delphi:

```
pDoc.Properties['FUZZY'] := 'TRUE';
if pDoc.FindKeyword['users', 'JOHN DOE'] > 0 then
[...]
Active Server Pages:
pDoc.Properties("FUZZY") = "TRUE"
if pDoc.FindKeyword("users", "JOHN DOE") > 0 then
[...]
```

The complete list of options is as follows:
Parameter Datatype Description Used in Conjunction with
  FUZZY Boolean Include in the result set entries similar to the original entry by using Soundex algorithm8 FindKeyword( )
MAX CHILDREN Number Sets the maximum bound on how many children of the current node are retrieved Children( )
PAGING INTERVAL Number To retrieve a subset of the result list, specifies the size of the subset Find( ), FindFirst( ), FindNext( )
PAGING START Number To retrieve a subset of the result list, specifies the starting element Find( ), FindFirst( ), FindNext( )
CACHEPATH String Location of the Meta Data cache file
  Sample use of 'PAGING INTERVAL' and 'PAGING START' options using Delphi:

```
... // pDoc is an olevariant, has been previously created, and has been
assigned a profile
object.
    [...]
    // retrieve ten results starting with the first one
    pDoc.Properties('PAGING START') := 1
    pDoc.Properties('PAGING INTERVAL') := 10
    if pDoc.Find['LAST_NAME = "DOE" AND
    FIRST_NAME="JOHN"'] > 0 then
    begin
        if pDoc.FindFirst[i] then
        repeat
            // the value of 'i' is the top root node satisfying the
            query
        until not pDoc.FindNext[i];
    end;
    // retrieve 5 results starting with 11th result
    pDoc.Properties('PAGING START') := 11
    pDoc.Properties('PAGING INTERVAL') := 5
    if pDoc.Find['LAST_NAME = "DOE" AND
    FIRST_NAME="JOHN"'] > 0 then
    begin
        if pDoc.FindFirst[i] then
        repeat
            // the value of 'i' is the top root node satisfying the
            query
        until not pDoc.FindNext[i];
    end;
```

Children

The Children function is an interface function similar to Find( ) and FindKeyword( ): a search operation is scheduled, and results are retrieved using FindFirst, FindNext and optionally FindResult. Given a node code, Children( ) returns all child node codes. This function is useful when navigating any element tree, regardless of the semantics of the data. This function is especially useful in conjunction with Find Result( ): the administration utility is making extensive use of this feature.

For example, using Delphi:
if pDoc.Children[NodeCode]>0 then
  if pDoc.FindFirst[iNode] then repeat
    [Use pDoc.FindResult[] to retrieve 'METATYPE', 'METANODENAME', 'ARRAYINDEX', 'ARRAYINDEX', 'HASCHILDREN', etc for display] until not objDatagate.FindNext[iNode];

In this example. iNode contains the node code of the ith child node of 'NodeCode'.

Nodeinformation

The NodeInformation function is an interface function similar to Children( ): a search operation is scheduled, and results are retrieved using FindResult( ). Given a node code, NodeInformation( ) returns TRUE if such a node exists, FALSE otherwise. In many instances, a great deal more than a node code is required to proceed with the data element. Hence, NodeInformation( ) should be used in conjunction with FindResult( ), as FindResult function provides most of the necessary information. For more details regarding the use of the FindResult function, refer to its section.

For example, using Delphi:
if pDoc.NodeInformation[NodeCode] then begin
  sCode:=pDoc.FindResult['METANODECODE'];
  sName:=pDoc.FindResult['METANODENAME']; end;

Findfirst, Findnext, Findresult

FindFirst and FindNext function allow for data retrieval after performing a call to Find, FindKeyword or Children functions. All Find, FindKeyword and Children return a count as the result of the query. If this result is 0, then the query operation did not return any result. If this count is greater than 0, then calls to FindFirst and FindNext are required. Typical code example for using FindFirst and FindNext is as follows:

For example, using Delphi:

```
If pDoc.FindKeyword['users', 'JOHN DOE'] > 0 then
    if pDoc.FindFirst[iNode] then
    repeat
        // iNode is the code of the element found
        [...]
    until not objDatagate.FindNext[iNode];
[...]
```

FindFirst and FindNext return TRUE if the data retrieval operation was successful, FALSE otherwise. In many instances, a great deal more than a node code is required to proceed with the data element. The FindResult( ) function provides most of the necessary information. After a FindFirst or FindNext, one can call the FindResult to find out about the data element value, meta node code and name, array index, data type, and if the data element has children. Possible values for the FindResult unique parameter are:

Parameter Description

MetaNodeCode Number—The meta node code corresponding to the element

MetaNodeName String—The meta node name corresponding to the element

ArrayIndex Number Variant value—Empty if the element is not an array element, or a number otherwise.

Value String—The data value of the element. Contains the string value of the element if the data type is not a long, otherwise contains '<long>'.

MetaType Number—Contains the data type of the element. Refer to the DATATYPES section to translate this number value to a string.

HasChildren Number—0, if not children, greater than 0 if any child(ren)

The function result is returned as a variant. For example, For example, using Delphi:

```
if pDoc.FindFirst[iNode] then
repeat
    varA := FindResult['METANODECODE'];
    varB := FindResult['ARRAYINDEX'];
    varC := FindResult['VALUE'];
    varD := FindResult['METATYPE'];
    varE := FindResult['METANODENAME'];
    varF := FindResult['HASCHILDREN'];
    [...]
until not objDatagate.FindNext[iNode];
[...]
```

Note that the FindResult( ) property is read only. Data can only be set using the Value( ) property.

Miscellaneous

Lasterror

The LastError( ) function reports the last errors that intervened during the calling application execution. Calling LastError( ) function will reset the error list.

ISA

This function accepts two parameters: 1) the string name of a meta node, and 2) a node code. The IsA( ) function will return true if the second parameter meta node code is either the meta node mentioned as first parameter, or a child meta node of the meta node mentioned as first parameter, otherwise returns false. For example, given the following meta node description:

A Top meta node
. . B Child of A
D Child of B
. . C Child of A

For a node n of meta node C, pDoc.IsA('A.C', n) is true, pDoc.IsA('A', n) is true and pDoc.IsA('A.B', n) is false. For a node n of meta node B, pDoc.IsA('A.B.D', n), pDoc.IsA('A.B', n), pDoc.IsA('A', n) all return true, while pDoc.IsA('C', n) or pDoc.IsA('A.C', n) return false.

SessionID

This function sets and retrieves Session ID.

Owner

This function returns user code of the currently logged-in user (via Profile.Authenticate( ) function).

Datatype

This function accepts one parameter—identifier string—and returns a number that corresponds to the identifier's datatype. See Datatype section of this document for the table providing the mapping between formal data types and data type number values.

Identifier

This function accepts a node code as a parameter and returns a full identifier string corresponding to that node code.

For example, using Delphi:

```
S := pDoc.Identifier[n];
//now, S equals 'patient.visit[2].DX[5].Date';
```

Topnode

This function accepts a node code as a parameter, and returns a node code of the topmost parent, i.e. the root node.

Code

This function is an inverse of the Identifier function. Given an identifier string, Code( ) function returns a node code.

ID

Instance data nodes are identified in two ways: by unique node codes, and by unique id numbers. The purpose of the later is to distinguish newly created nodes that have not been saved yet (via Save( ) function) and thus do not yet have a node code. The ID( ) function accepts identifier string as a parameter and returns that node's corresponding ID number.

Identifieritemcount

This function returns number of terms in the identifier string.

For example, using Delphi:
iCount:=pDoc.IdentifierItemCount['patient.visit[2].DX[5].Date'];
//now, iCount equals 4

Identifieritem

This function is used in conjunction with the IdentifierItemCount( ) function. ItentifierItem( ) accepts two parameters: identifier string, and index; and returns a single term at the given index from the identifier string.

For example, using Delphi:
s:=pDoc.IdentifierItem ['patient.visit[2].DX[5].Date', 3];
// now, s equals 'Date'

Isempty

Geven identifier string, IsEmpty( ) returns TRUE if the identifier hold no value.

Asmetacode

This function accepts identifier string as a parameter and returns code of the Meta Data node that represents the identifier.

Ismodified

Geven identifier string, IsModified( ) returns TRUE if the identifier value has changed since it was last saved.

Link

This function accepts two parameters: identifier string and node code. The identifier string specifies a virtual list to which the node (specified by the node code) is to be added. The node can exist within the same tree as the virtual list or come from a different tree. Link( ) function establishes a pointer from the virtual list to the node, and returns TRUE if the operation was successful.

For example, to achieve linking between 'Person' and 'Provider' shown in the diagram above, the following Delphi code is written:

```
IfpDoc.Open[11] and pDoc.SetLock['Person'] then
    PDoc.Link['Visit_Provider[ ]', 152];
    PDoc.Save;
    Pdoc.CloseLock['Person'];
    PDoc.Close;
End if
```

Unlink

This function accepts two parameters: identifier string and index. The identifier string specifies a virtual list; and index specifies the array element to be removed. Unlink( ) function does not erase the node at index; it simple removes the reference/pointer from the virtual list to the node.

Archivecount

ADM keeps an audit trail of all the changes in the instance data. Any create, delete, and update operations are recorded and flagged with the id of the user performing the change. ArchiveCount( ) function accepts identifier string as a parameter, and returns the number of changes made to instance data denoted by the identifier string.

Archive

This function is used in conjunction with the Archive-Count( ) function. Archive( ) function accepts three parameters: identifier string, index, and archive property. The identifier string specifies the instance data for which the audit trail is retrieved; the index indicates a specific audit in the list of changes; and archive property denotes a specific information to be retrieved, such as 'VALUE', 'DATE', or 'USER'.

Parameter Description

VALUE Returns the value of the node during the update
DATE Returns the date when the node update occurred
USER Returns the identification of the user that administered the node update For example, consider that 'patient.lastname' was created with value 'Smith'; then changed to 'Jones'; and after a while changed to 'Ford'.

Using Delphi:

```
iCount := pDoc.ArchiveCount['patient.lastname']; // iCount = 3
for I :=0 to iCount − 1 do
begin
    sValue := Archive['patient.lastname', I, 'VALUE'];   // if I = 0,
                                                         then
                                                         // sValue =
                                                         'Smith', etc.
    sDate := Archive['patient.lastname', I, 'DATE'];
    sUser := Archive['patient.lastname', I, 'USER'];
end;
```

RTF

This function returns RTF string illustrating all of the instance data in the data source. With colors and indents, the RTF string depicts data types and relationships among the data elements.

Function Reference
SetProfile
Description Function

Set a connection between the Profile object and current IDatagate new instance.

Syntax Procedure SetProfile(Profile: Iprofile);
Example DELPHI:

```
var
    pProfile, pDoc: OLEVariant;
begin
    try
        pProfile := CreateOLEObjects('ADM.Profile');
        if pProfile.SetConnection['test', 'scott', 'tiger', 'host'] and
           pProfile.Authenticate[1, '', ''] then
        try
            pDoc:=CreateOLEObject('ADM.Datagate');
            pDoc.SetProfile(pProfile)
            [...]
            pDoc:= unassigned;
        except
            [...]
        end;
        pProfile := unassigned;
    except
        [...]
    end;
end;
```

Open
Description Function

Initializes the COM objects with the data stored into the Adaptive Data Manager starting at root element intNodeCode.

Note that not all data is loaded: This object was designed using a 'load on demand' principle, where data is only fetched from the database when requested for the first time.

Note that a connection must have been established before calling Open. All loaded data is by default Read Only. Some data may have been previously locked, and consequently may be set as Read & Write.

Returns TRUE if successful, FALSE otherwise. If unsuccessful, possible reasons are failed database connection, invalid node code. Check the LastError function content for the cause of failure.

Syntax function Open(intNodeCode: longint): boolean

Example This example shows all steps to opening a record within ADM.

The value 123456 is a node code, and is a the code for a root node code. Typically this value will be returned as part of a search (using Find or FindKeyword functions).

Delphi:

```
var
    pProfile, pDoc: OLEVariant;
begin
    try
        pProfile := CreateOLEObjects('ADM.Profile');
        if pProfile.Open['Provider=OraOLEDB.Oracle.1;Persist Security
Info=False;User
ID=test;Data Source=tiger', 'test', 'scott', 'host'] and
pProfile.Authenticate[1, '', ''] then
            try
                pDoc:= CreateOLEObject('ADM.Datagate');
                pDoc.SetProfile(pProfile)
                if pDoc.Open(123456) then
                begin
                    [...]
                end;
                pDoc.Close;
                pDoc:= unassigned;
            except
                [...]
            end;
            pProfile := unassigned;
        except
            [...]
        end;
end;
```

Close

Description Procedure

Resets the data content of the IDatagate instantiated interface. Note that all locks that may have previously set on the data content will not be affected. Refer to CloseLock for removing locks. Any elements that may have been modified will not be saved to the data store.

This function always returns TRUE.

Syntax Procedure Close;

Save

Description Function

Saves the data content of the IDatagate instantiated interface. Only non Read/Only elements (i.e. only elements that were successfully locked) will be saved to the data store.

Returns TRUE if successful, FALSE otherwise. If unsuccessful, check the LastError function content for the cause of failure.

Note that all locks are not removed after the Save operation.

Syntax function Save: boolean;

Delete

Description Function

This function allows elements of opened records to be deleted, by specifying an identifier; all elements child of that identifier will be deleted as well. The identifier is any legal identifier. Note that the parent of the mentioned identifier must be read/write state: refer to the SetLock( ) function.

This function returns TRUE if successful, FALSE otherwise. If unsuccessful, check the LastError function content for the cause of failure.

Syntax function Delete(strIdentifier: String): boolean;

SetLock

Description Function

Sets a database lock on the database node corresponding to the identifier. If successful, the identifier becomes Read & Write. Note that all identifier child elements are locked as well. The lock is based on the owner and session's code, thus allowing the same owner (i.e. user) to lock different elements for different sessions. Typically, the session will either be an IIS web server session ID, or an Oracle session ID. The owner and session are established when creating the parent IProfile interface, that is later communicated to the current IDatagate interface..

This function returns TRUE if successful, FALSE otherwise. If unsuccessful, check the LastError function content for the cause of failure.

Syntax function SetLock(strIdentifier: String): boolean;

CloseLock

Description Function

Closes an identifier lock. The identifier data is reset Read Only mode. This function returns TRUE if successful, FALSE is the lock could get established.

Setting a lock will be unsuccessful if another user already has a lock the requested data element. Check the LastError function content for the cause of failure. Check current locks using the ADM Administration Utility, Lock Tab, to list existing locks.

Syntax function CloseLock(strIdentifier: String): boolean;

Find,

FindKeyword,

Description Function

The Find function allows for queries over the entire Adaptive database model. For example, one could query all node trees where node of meta node type 'Last Name' is 'Doe', and node of meta node type 'First Name' is 'John'. The logic of this function is based on sets, and thus allows for set intersections, differences and unions.

The FindKeyword( ) function allows for keyword or concept searches for a specified portion of the data store or for the whole data store. For example, if the Adaptive Data Manager data store has data elements about users and media articles, then one could look for all articles making references to 'Chest' and 'Pain', within the 'Media[]' branch. Note that the search is case insensitive Find( ) and FindKeyword( ) functions will prepare the query and return the number (count) of entries that matched the query. The FirstFirst( ) and FindNext( ) functions will respectively return the first entry and the following entries. Note that one can loop through all results several times using FindFirst to reset the result index without having to re-submit Find.

Check the Properties( ) function for possible behavior options.

☐ Note that only data saved into the data store will be queried using this method. In order to have the data stored in memory also queried, Save the data first before performing a query.

Syntax function Find(const strLookup: WideString): Integer; function FindKeyword(const strIdentifier, strLookup: WideString): Integer;

Example DELPHI:

```
Var
    b: boolean;
    i: olevariant;
[...]
if pDoc.Find['LAST_NAME = "YOUNG" AND
FIRST_NAME="ANDRE"'] > 0 then
begin
    pDoc.FindFirst[i];
    repeat
        // the value of 'i' is the top root node tisfying the
            query
    until not pDoc.FindNext[i];
end;
```

Children
Description Function
Return the list of child elements for the 'node' parent element. The value for node is a node.node_code.
The Children( ) function will prepare the query and return the number (count) of child elements for 'Node'. The FirstFirst( ) and FindNext( ) functions will respectively return the first entry and the following entries. Note that one can loop through all results several times using FindFirst( ) to reset the result index without having to re-submit Children( ). Check the Properties( ) function for possible behavior options.
Syntax Function Children(Node: variant): longint
NodeInformation
Description Read-Only Property
This function allows returning database information about an existing node.
Syntax property Identifier[intNodeCode: Integer]: String
FindFirst,
FindNext
Description Function
Allows retrieval of node elements after Find( ), FindKeyword( ) or Children( ) functions. FindFirst( ) and FindNext( ) return TRUE if the operation was successful, FALSE otherwise. If unsuccessful, check the LastError function content for the cause of failure
Example DELPHI:

```
var
    n, i: longint;
[. . .]
    n := pDoc.Children['PATIENT.VISIT[]'];
    if pDoc.FindFirst[i] then
    repeat
        // the value of 'i' is the top root node satisfying the query
    until not pDoc.FindNext[i];
```

Syntax Function FindFirst(out intRootCode: OLEVariant): WordBool;
Function FindNext(out intRootCode: OLEVariant): WordBool;
FindResult
Description Function
The FindResult( ) function is used in conjunction with FindFirst( ) and FindNext( ) functions. FindFirst( ) and FindNext( ) functions only return a node code; the FindResult( ) function allows to get additional information to the code returned by FindFirst( ) and FindNext( ).
METANODECODE Number—The meta node code corresponding to the element
METANODENAME String—The meta node name corresponding to the element
ARRAYINDEX Number Variant value—Empty if the element is not an array element, or a number otherwise.
VALUE String—The data value of the element. Contains the string value of the element if the data type is not a long, otherwise contains '<long>'.
METATYPE Number—Contains the data type of the element. Refer to the DATATYPES section to translate this number value to a string.
HASCHILDREN Number—0, if not children, greater than 0 if any child(ren)
Syntax Function FindResult(Entry: OLEVariant): OLEVariant;
Properties
Description Property The Properties property allows Datagate options to be set or accessed. Current options are:
'FUZZY': Allows Soundex search mode for FindKeyword function
'MAX CHILDREN': Limits the maximum number of children that can be retrieved using the Children( ) function
'PAGING INTERVAL': Allows to retrieve a subset of the result list by setting the size of the subset
'PAGING START': Allows to retrieve a subset of the result list by specifying the starting element
'CACHEPATH': Specifies the location of the Meta Data cache file
Syntax Property Properties(const strOption: WideString): OleVariant;
SessionID
Description Read-Only Property
Returns the SessionID value previously set by the Open function. If used previously to any Open function call, returns −1.
Syntax Function SessionID: longint;
Owner
Description Read-Only Property
Returns the Owner value previously set by the Open function. If used previously to any Open function call, returns −1.
Syntax Function Owner: longint;
XML
Description Read & Write Property
This property allows for all data for the current root node to be exported as XML, or for a block of XML to be imported either under the current root node or under any node element (use the sStart value to specify the start node; leave this value to start under the root node). Check the LastError content for possible failure.
Syntax Property XML[sStart: String]: String;
Value
Description Read & Write Property
This property allows setting or getting a value for an identifier.
Note that the transferred value is a variant, and thus may cause conversion errors. Check the LastError content for possible failure.
Syntax Property Value[strIdentifier: String]: Variant
Add
Description Read-Only Property
This property allows for next array records to be created into an array. This property returns the index of the next created array record. The identifier specified into the function must be an array (thus have the [ ] notation.)
This function will return −1 in case of failure; in this case, check the content of LastError.
Syntax Property Add[strIdentifier: String]: integer
Count
Description Read-Only Property
This property returns the number of child nodes if the element specified by strIdentifier is an array. If the identifier element has a discrete data type (string, integer, real, date, or boolean) then accessing this property will cause an exception. Check the LastError content for possible failure.
Syntax Property Count[strIdentifier: String]: longint
IsA
Description Read-Only Property
This function checks if the instance data referred to by intNodeCode is of type meta data strIdentifier. This function returns TRUE if the operation was successful, FALSE otherwise. Check the LastError content for possible failure.

Syntax function IsA(const strIdentifier: WideString; intNodeCode: Integer):
    WordBool;
IsReadOnly
Description Read-Only Property
    This property returns TRUE if an identifier is Read & Write, FALSE if Read Only. Refer to the Lock function for setting an identifier as Read & Write. Check the LastError content for possible failure.
Syntax Property IsReadOnly[strIdentifier: String]: boolean
IndexOf
Description Read & Write Property
    This property sets or gets the current index for an array node. Check the LastError content for possible failure.
Syntax Property IndexOf[strIdentifier: String]: longint
Datatype
Description Read-Only Property
    This property returns the data type of a node as an integer. Possible values are number for String, Integer, Real, Date, Long String, Boolean, Array, Array Record and Virtual Array. Note that the meta-data data type cannot be altered through this interface, and can only be managed using the ADM Administration Utility.
    Check the LastError content for possible failure.
Syntax Property Datatype[strIdentifier: String]: longint
LastError
Description Read-Only Property
    This property returns the error log as text. Calling this function resets the error log content. All errors met until the LastError function call are part of the error log.
Syntax Property LastError: Variant
CurrentIndex
Description Write-Only Property
    This property sets the identifier specified as the argument of this function to be the current index. Check the LastError content for possible failure. Note that this function was designed to work in conjunction with the TopNode( ) and Identifier( ) functions.
Syntax property CurrentIndex: String
Identifier
Description Read-Only Property
    This function returns a fully defined identifier given the node code specified as unique parameter. This function is especially useful for indexing and searching purposes.
Syntax property Identifier[intNodeCode: Integer]: String
TopNode
Description Read-Only Property
    For any node element code, this function returns the top element node code. This function is usually used by passing the node element code obtained from FindFirst( ) or FindNext( ). from Check the LastError content for possible failure.
Syntax property TopNode[intNodeCode: Integer]: Integer
Code
Description Read-Only Property
    This function returns the node element associated with any identifier. This function will return −1 if the element has not been saved to the database yet.
Syntax Property Code[strIdentifier: String]: OleVariant
Order
Description Read/Write Property
    This function sets and returns the current subscript order of an array element. If the new subscript value is out of legal array bound, then no action is taken.
Syntax property Order[strIdentifier: WideString]: Integer
IdentifierItem, IdentifierItemCount
Description Read Only Property These functions are 'helper' functions and allow for identifier string manipulations. For any legal identifier strings, the IdentifierItemCount( ) function returns the number of segments within the string, and IdentifierItem( ) returns the segment as a string.
Syntax Function IdentifierItem(strIdentifier: String; Index: longint): String;
Function IdentifierItemCount(strIdentifier: String): longint;
ID
Description Read Only Property Instance data nodes are identified in two ways: by unique node codes, and by unique id numbers. The purpose of the later is to distinguish newly created nodes that have not been saved yet (via Save( ) function) and thus do not yet have a node code. The ID( ) function accepts identifier string as a parameter and returns that node's corresponding ID number.
Syntax Function ID(strIdentifier: String): longint;
IsEmpty
Description Read/Wirte Property
    Given identifier string, IsEmpty( ) function returns TRUE if the identifier holds value.
    Set IsEmpty( ) to TRUE to clear the identifier of its value.
Syntax Function IsEmpty(strIdentifier: String): boolean;
IsModified
Description Read Only Property
    Given identifier string, IsModified( ) function returns TRUE if the identifier value has changed since it was last saved.
Syntax Function IsModified(strIdentifier: String): boolean;
AsMetaCode
Description Read Only Property
    Returns a code of the Meta Data node that represents the identifier.
Syntax Function AsMetaCode(strIdentifier: String): longint;
Link
Description Write Only Property
    The identifier string specifies a virtual list to which the node (specified by the node code) is to be added. The node can exist within the same tree as the virtual list or come from a different tree. Link( ) function establishes a pointer from the virtual list to the node, and returns TRUE if the operation was successful.
Syntax Function Link(strIdentifier: String; iNodeCode: longint): boolean;
Unlink
Description Write Only Property
    The identifier string specifies a virtual list; and index specifies the array element to be removed. Unlink( ) function does not erase the node at index; it simple removes the reference/pointer from the virtual list to the node.
Syntax Function Unlink(strIdentifier: String; iIndex: longint): boolean;
ArchiveCount
Description Read Only Property
    ADM keeps an audit trail of all the changes in the instance data. Any create, delete, and update operations are recorded and flagged with the id of the user performing the change. ArchiveCount( ) function accepts identifier string as a parameter, and returns the number of changes made to instance data denoted by the identifier string.
Syntax Function ArchiveCount(strIdentifier: String): longint;
Archive
Description Read Only Property
    This function is used in conjunction with the ArchiveCount( ) function. Archive( ) function accepts three parameters: identifier string, index, and archive property. The identifier string specifies the instance data for which the audit trail is retrieved; the index indicates a specific audit in the list of changes; and archive property denotes a specific information to be retrieved, such as 'VALUE', 'DATE', or 'USER'.

'VALUE': value of the node during a particular update
'DATE': date when the node update occurred
'USER': identification of the user that administered the update operation Syntax Function Archive(strIdentifier: String; iIndex: longint): OleVariant;
RTF
Description Read Only Property This function returns RTF string illustrating all of the instance data in the data source. With colors and indents, the RTF string depicts data types and relationships among the data elements.

Syntax Function RTF: String;

ADM.Index

Introduction

ADM.Index is the interface, supporting document indexing, under the Adaptive Data Manager paradigm. Indexing is declared at the meta data level in the form of indexing flags, and any creation of corresponding instance data will trigger the creation of entries into a 'request for data processing' queue. This queue lists all ADM.Datagate elements that are waiting for indexing. Indexing consists of analyzing each pending element and computing or establishing the relevant set of keywords and/or concepts that best describe the element. The resulting keywords will be sent to an index storage that will be accessed in turn by the ADM.Datagate interface.

This interface provides two basic functions:

Access to the data processing queue.

ADM.Index provides all means to query the data processing queue, lock entries for processing and remove from the queue processed items.

Access to the indexing storage.

ADM.Index provides all means to query existing concepts and keywords, add new concepts and keywords, or clear existing entries.

ADM.INDEX TOOLS AND FUNCTIONS
QUEUE MANAGEMENT
QUEUECOUNT, QUEUE, LOCKQUEUE, UNLOCKQUEUE, CLOSEQUEUE,
QUEUEVALUE

The Queue and QueueCount provide the means to browse existing queue entries. A queue entry contains a reference to a particular element from the ADM.Datagate storage, as well as a creation date, and possibly a reference to a user processing this entry. The QueueValue function retrieves the stream of text that is queued to be concept/keyword indexed. Eventually, the LockQueue, UnlockQueue and CloseQueue functions provide queue management: LockQueue provides exclusive access to a queue element, UnlockQueue releases the exclusive access, while CloseQueue removes the element from the queue.

The current state of the queue is buffered internally into the ADM.Index object. Each time an access is made to QueueCount, the buffer is refreshed.

A typical example of use of these functions would be as follows:

For example, using Delphi:

```
// pProfile Created
[...]
pIndex := CreateOLEObject('ADM.INDEX');
pIndex.SetProfile(pProfile)
for i := 0 to pIndex. QueueCount – 1 do
```

-continued

```
    if pIndex.Queue[i, iNode, iUserCode, datCreated, intState] and
        pIndex.LockQueue[iNode, kiUSER] then
    begin
        if pIndex.QueueValue[iNode, ws] then
        [. . .] // Processing happen here for making keywords.
        pIndex.CloseQueue[iNode, kiUSER];
    end;
pIndex := unassigned;
```

In other words, this example shows the queue to be opened (SetProfile( ), QueueCount( )) and browsed (Queue( )), each queue element is locked for exclusive use (LockQueue( )), the value of a queue element is accessed (QueueValue( )), and the queue element is removed from the queue (CloseQueue( )).

☐ Note this model supports one or more threads simultaneously processing data.

Wordindexcount, Wordindex, Clearwordindex, Addwordindex

The WordIndex( ) and WordIndexCount( ) functions provide the means to browse existing index entries for a specific ADM.Datagate element. Note that the list of index keywords and concepts for a specific element is buffered internally. This buffer is refreshed each time the WordIndexCount( ) function is accessed. An index entry contains a reference to a particular element from the ADM.Datagate storage, as well as a source and a text. The source identifies what concept domain was used to create the index text entry. For example, valid domains are FREETEXT, ICD, CPT, etc. The ClearWordIndex( ) function removes existing entries for a ADM.Datagate element, while AddWordIndex( ) creates new index entries.

Miscellaneous

Lasterror

The LastError( ) function reports the last errors that intervened during the calling application execution. Calling LastError( ) function will reset the error list.

Setprofile

Instantiating the COM object is the first step to being able to data access. The second step consists in establishing a connection to the data store, i.e. the relational database storage. This is effective using the SetProfile( ) function, by connection this instance of the IIndex interface to a previously created instance of IProfile interface.

Function Reference
QueueCount
Description Read-Write Property
Returns the current number of data processing queue entries.
Syntax property QueueCount: Integer;
Queue
Description Read-Write Property
Returns all elements from any data processing queue entry.
Syntax property Queue[intIndex: Integer; out intNodeCode: Integer; out intUserCode: Integer; out datCreated: OleVariant; out intState: OleVariant]: boolean
LockQueue, UnlockQueue, CloseQueue
Description Read-Write Property
Refer to the ADM.Datagate Tools and Functions
Queue Management
Syntax property LockQueue[intNodeCode: Integer; intUserCode: Integer]: boolean
property UnlockQueue[intNodeCode: Integer; intUserCode: Integer]: boolean property CloseQueue[intNodeCode: Integer; intUserCode: Integer]: boolean QueueValue Description Read-Write Property Retrieves the text content of a queue entry to be indexed.

Syntax property QueueValue[iNodeCode: Integer; out wsString: WideString]: boolean WordIndexCount Description Read-Write Property Retrieves the word index count for an ADM.DATAGATE element.

Syntax property WordIndexCount[intNodeCode: Integer]: Integer

WordIndex

Description Read-Write Property

Retrieves any index element for a ADM.Datagate element.

Syntax property WordIndex[intNodeCode: Integer; intIndex: Integer; out strSource: OleVariant; out strCode: OleVariant; out intWeight: Integer]: boolean ClearWordIndex Description Read-Write Property Clear up any word index for a specific ADM.Datagate element.

Syntax property ClearWordIndex[intNodeCode: Integer]: boolean

AddWordIndex

Description Read-Write Property

Add a new word index for a specific ADM.Datagate element.

Syntax property AddWordIndex[intNodeCode: Integer; strSource: OleVariant; strCode: OleVariant; intWeight: Integer]: boolean SetProfile Description Function Set a connection between the Profile object and th current IDatagate new instance.

Syntax Procedure SetProfile(Profile: IProfile);

Example DELPHI:

```
Var
    pProfile, pObj: OLEVariant;
begin
    // pProfile is created here or has already been created
    [...]
    try
        pObj := CreateOLEObject('ADM.INDEX);
        pObj.SetProfile(pProfile);
        [...]
        pObj := Unassigned;
    except
        raise;
    end;
end;
ACTIVE SERVER PAGES:
<%@ Language=VBScript %>
<%
Option Explicit
On Error Resume Next
Dim pObj
Set pObj = Server.CreateObject("ADM.INDEX")
pObj.SetProfile(pProfile);
[...]
Set pObj = nothing
%>
```

LastError

Description Read-Only Property

This property returns the error log as text. Calling this function resets the error log content. All errors met until the LastError function call are part of the error log.

Syntax Property LastError: Variant

ADM.Dictionary

Introduction

The ADM.Dictionary COM object provides an access to the standard Adaptive Data Manager lookup dictionary. All lookup dictionary entries are classified using a type: for example 'Gender', 'Age Group', etc. Each dictionary entry is then made a code and a description. This object provides different methods for accessing lists of codes and descriptions for a specific dictionary type, or for retrieving the description for a specific dictionary type and code.

ADM.Dictionary Tools and Functions

Establishing a Connection to a Data Store

Instantiating the COM object is the first step to being able to data access. The second step consists of establishing a connection to the data store, i.e. the relational database storage. This is effective using the SetProfile( ) function.

Examples:

For example, using Delphi:

```
Var
    pDoc: Idictionary;
[...]
pDoc := CreateCOMObject('ADM.Dictionary');
pDoc.SetProfile(pProfile) ;
[...]
pDoc := nil;
Active Server Pages:
dim pDoc
pDoc = CreateOLEObject("ADM.Dictionary")
pDoc.SetProfile(pProfile)
[...]
pDoc = nothing
```

Setting up the IDictionary interface instance with a IProfile interface establishes a connection to the ADM data store. The connection to the data store is closed when the object is de-instantiated.

Retrieving Lookup Data

ID, Count, Children, Properties

ADM.Dictionary lookup data is usually retrieved using two identifiers: one identifier for the dictionary group, and one for the dictionary item within the group. To find the identifier for a particular group or item, ID( ) function is used. Count( ) function retrieves the number of items in a group. To find the identifier for a particular item in a group, Children( ) function is called. And finally, to set and retrieve group and item properties (name, description), Properties( ) method is used.

For example, there may exist a dictionary group called 'Marital Status'. The group holds five items: 'Single', 'Married', 'Separated', 'Divorced', 'Widowed'.

Dictionary's name is 'MARITAL_STATUS', description is 'Marital Status'. First item's name is 'S', and the description is 'Single'. Second item's name is 'M', and the description is 'Married', etc. To populate a combo-box or a listbox, the following Delphi code can be used:

```
Var
    lGroupId: longint;
    lItemId: longint;
    lItemCount: longint;
    i: longint;
    SDescription: String;
[...]
lGroupId := pDoc.ID['MARITAL_STATUS'];
```

-continued
```
    IItemCount := pDoc.Count[iGroupId];
    for i := 0 to iItemCount − 1 do
    Begin
        IItemId := pDoc.Children[iGroupId, I];
        SDescription := pDoc.Properties[iItemId, 'DESCRIPTION'];
        Listbox.Add(sDescription);
    End;
    Using Active Server Pages:
    Dim iGroupId, iItemId, iItemCount
    Dim I
    Dim sDescription
    [. . .]
    IGroupId = pDoc.ID("MARITAL_STATUS")
    IItemCount = pDoc.Count(iGroupId)
    for i = 0 to iItemCount − 1
        IItemId = pDoc.Children(iGroupId, I)
        SDescription = pDoc.Properties(iItemId, "DESCRIPTION")
        Response.write sDescription
    next
```

In both examples, the i subscript is the index for getting all code/description pairs. Once group id and/or item id are retrieved using ID( ) and/or Children( ) methods, dictionary group and item properties can be accessed and set via the Properties( ) function. Properties( ) function accepts two parameters: id, and property option. Options for the second parameter are:

Parameter Description
ID Read Only. Returns number denoting group's or item's unique id.
NUMERIC_ONLY Returns the date when the node update occurred ACTIVE_FLAG Returns TRUE if the group or item is active/enabled. FALSE otherwise.
POSITION Returns the order in which items within a group are retrieved.
NAME Returns the name or the group or item.
DESCRIPTION Returns the description of the group or item.

Countbycodename, Propertiesbycodename, ValuesbyCodename

Besides the lookup functions described in the previous section, there also exists a second set of functions. This set of functions is convenient when dictionary's group code or name is already known (and in some cases item code or name). Here, 'code' refers not to the group's or item's id, but to the unique code by which the dictionary entry is identified in the datasource's dictionary tables. To retrieves the number of items in a given group, CountByCodeName( ) is used. ValuesByCodeName( ) sets and retrieves item properties based on that item's index within the group. And, PropertiesByCodeName( ) sets and retrieves item properties when item's code or name is known. These lookup functions have names ending in 'ByCodeName' because they can accept either the code or the name as a parameter; so it is helpful to think of these functions as 'ByCodeORName'. The functions interpret whether the parameter is numeric or alphanumeric. If the parameter is numeric, then it is assumed that the parameter represents a datasource code. If the parameter is alphanumeric, then it stands for the group/item name. ☐ Note that when numeric names are used for item names (e.g. '0' for Male gender, and '1' for Female), the lookup functions will interpret them as datasource codes.

For example, using Delphi:

```
    Var
        IItemCount: longint;
        i: longint;
        sDescription, sDescription_M: String;
    [. . .]
    IItemCount := pDoc.CountByCodeName['MARITAL_STATUS'];
    for i := 0 to iItemCount − 1 do
    Begin
        SDescription := pDoc.ValuesByCodeName
    ['MARITAL_STATUS', i,
    'DESCRIPTION'];
        Listbox.Add(sDescription);
    End;
    sDescription_M := pDoc.PropertiesByCodeName
    ['MARITAL_STATUS', 'M',
    'DESCRIPTION'];
    Using Active Server Pages:
    Dim iItemCount
    Dim I
    Dim sDescription, sDescription_M
    [. . .]
    IItemCount = pDoc.CountByCodeName
    ("MARITAL_STATUS")
    for i = 0 to iItemCount − 1 do
    Begin
        SDescription := pDoc.ValuesByCodeName
    ("MARITAL_STATUS", i,
    "DESCRIPTION")
        Response.write sDescription
    Next
    sDescription_M = pDoc.PropertiesByCodeName
    ("MARITAL_STATUS", "M",
    "DESCRIPTION")
```

Adding, Deleting, and Updating Element Values

ADD

The Add( ) function creates new dictionary groups or items. The function accepts one parameter—group id—and returns the id of the newly created element. To create a new dictionary group, Add( ) is called with '−1' (e.g. pDoc.Add [−1]). To create a new item within a group, Add( ) is called with that group's id (e.g. pDoc.Add[iGroupId]).

Delete

The Delete( ) function accepts one parameter—id of the elements that is to be deleted. The parameter is either a group id or an item id. In case of group id, the whole group and its elements are deleted.

Properties, Propertiesbycodename, Valuesbycodename

To update values of the existing elements, Properties( ), PropertiesByCodeName( ), and ValuesByCodeName( ) functions are used.

For example, using Delphi:
pDoc.Properties[iGroupId, 'DESCRIPTION']:='Patient Marital Status';
pDoc.ValuesByCodeName['MARITAL_STATUS', i, 'DESCRIPTION']:='Not Married';
pDoc.PropertiesByCodeName['MARITAL_STATUS', 'M', 'DESCRIPTION']:="Not Married";

Save

The Save( ) function writes all the changes to the datasource.

Set Operations

XML

Data elements can be accessed or set, either in parts or in entirety, using the XML property.

Miscellaneous

Refresh

The Refresh( ) function dismisses any changes made to the ADM.Dictionary since the last save operation, and reloads dictionary elements from the datasource.

Lasterror

The LastError( ) function reports the last errors that intervened during the calling application execution. Calling LastError( ) function will reset the error list.

Ismodified

IsModified( ) returns TRUE if any dictionary values have changed since the dictionary was last saved.

Function Reference
SetProfile
Description Function

Set a connection between the Profile object and the current IDictionary new instance.
Syntax Procedure SetProfile(Profile: IProfile);
Example DELPHI:

```
Var
    pProfile, pObj: OLEVariant;
begin
    // pProfile is created here or has already been created
    [...]
    try
        pObj := CreateOLEObject('ADM.DICTIONARY');
        pObj.SetProfile(pProfile);
        [...]
        pObj := Unassigned;
    except
        raise;
    end;
end;
ACTIVE SERVER PAGES:
<%@ Language=VBScript %>
<%
Option Explicit
On Error Resume Next
Dim pObj
Set pObj = Server.CreateObject("ADM.DICTIONARY")
pObj.SetProfile(pProfile);
[...]
Set pObj = nothing
%>
ID
Description         Read-Only Property
Returns a unique identifier for a particular group or item.
Syntax              property ID[strName: String]: longint
Count
```

Description Read-Only Property

Returns the number of items in a given group (specified by the group id).
Syntax property Count[iID: longint]: longint
Children
Description Read-Only Property Returns the identifier for a particular item in a group, Children( ) function. First parameter is the group id, and second parameter is item's index within the group.
Syntax property Children[iID, iIndex: longint]: longint;
Properties
Description Read-Write Property Given an element id (group or item), sets or retrieves element's values.
Property options are:
Parameter Description
ID Read Only. Returns number denoting group's or item's unique id.
NUMERIC_ONLY Returns the date when the node update occurred ACTIVE_FLAG Returns TRUE if the group or item is active/enabled. FALSE otherwise.
POSITION Returns the order in which items within a group are retrieved.
NAMEReturns the name or the group or item.
DESCRIPTION Returns the description of the group or item.
Syntax property Properties[iID: longint; strProperty: String]: Variant
CountByCodeName
Description Read-Only Property Returns the number of items in a given group (specified by the group code or name).
Syntax property CountByCodeName [GroupCodeOrName: Variant]: longint;
ValuesByCodeName
Description Read-Write Property Given group code or name, and item's index within the group, ValuesByCodeName( ) method sets or retrieves element's property values.
Property options are:
Parameter Description
ID Read Only. Returns number denoting group's or item's unique id.
NUMERIC_ONLY Returns the date when the node update occurred ACTIVE_FLAG Returns TRUE if the group or item is active/enabled. FALSE otherwise.
POSITION Returns the order in which items within a group are retrieved.
NAMEReturns the name or the group or item.
DESCRIPTION Returns the description of the group or item.
Syntax property ValuesByCodeName[GroupCodeOrName: Variant; iIndex: longint; strProperty: string]: Variant
PropertiesByCodeName
Description Read-Write Property Given group code or name, and item code or name, PropertiesByCodeName( ) method sets or retrieves element's property values.
Property options are:
Parameter Description
ID Read Only. Returns number denoting group's or item's unique id.
NUMERIC_ONLY Returns the date when the node update occurred ACTIVE_FLAG Returns TRUE if the group or item is active/enabled. FALSE otherwise.
POSITION Returns the order in which items within a group are retrieved.
NAMEReturns the name or the group or item.
DESCRIPTION Returns the description of the group or item.
Syntax property PropertiesByCodeName [GroupCodeOrName: Variant; ItemCodeOrName: Variant; strProperty: string]: Variant
Add
Description Write-Only Property The Add( ) function creates new dictionary groups or items. The function accepts one parameter—group id—and returns the id of the newly created element. To create a new dictionary group, Add( ) is called with '−1' (e.g. pDoc.Add [−1]). To create a new item within a group, Add( ) is called with that group's id (e.g. pDoc.Add[iGroupId]).
Syntax function Add[iID: longint]: longint;
Delete
Description Write-Only Property The Delete( ) function accepts one parameter—id of the elements that is to be deleted. The parameter is either a group id or an item id. In case of group id, the whole group and its elements are deleted.
Syntax function Delete[iID: longint]: Boolean;
Save
Description Write-Only Property Writes all the changes to the datasource.
Syntax function Save: Boolean;
XML
Description Read-Write Property Data elements can be accessed or set, either in parts or in entirety, using the XML property.

Syntax property XML[sGroupName: String]: String;
Refresh
Description Read-Only Property
Dismisses any changes made to the ADM.Dictionary since the last save operation, and reloads dictionary elements from the datasource.
Syntax function Refresh: boolean;
IsModified
Description Read-Only Property
Returns TRUE if any dictionary values have changed since the dictionary was last saved.
Syntax function IsModified: Boolean;
LastError
Description Read-Only Property
This property returns the error log as text. Calling this function resets the error log content. All errors met until the LastError function call are part of the error log.
Syntax Function LastError: String;

APPENDIX A:

COM Interfaces Calling Reference

A COM object can be instantiated using three basic distinct solutions:

Using Ole:

This is usually referred to as 'late binding'; the code makes reference to objects; these references will be resolved when the code is just about to execute. This is extremely flexible but rather dangerous, as the underlying COM object may change and disrupt applications using late binding.

For Example, using Delphi:

```
var
    a: OLEVariant;
begin
    a := CreateOLEObject('ADM.PROFILE');
        if a.Open['Provider=OraOLEDB.Oracle.1;Persist Security
            Info=False;User
ID=test;Data Source=tiger', 'test', 'scott', 'host'] and
a.Authenticate[1, '', ''] then
            [...]
        a := unassigned;
end;
```

Note that it is important to de-instantiate the OLE object after use, by writing under Delphi a:=unassigned; or by writing under ASP a=nothing Use Com and Type Libraries This is usually referred to as 'early binding'. The compiler can check that COM object references are actually legal, and thus can display compilation errors, while creating the application executable. For Example, using Delphi:

```
var
    a: IProfile;
begin
    a := CreateComobject(CLASS_Profile) as Profile;
        if a.Open['Provider=OraOLEDB.Oracle.1;Persist Security
            Info=False;User
ID=test;Data Source=tiger', 'test', 'scott', 'host'] and
a.Authenticate[1, '', ''] then
            [...]
        a := nil;
end;
```

Again, note that it is important to de-instantiate the COM object after use, by writing under Delphi a:=nil;

A variant to this solution is to use DCOM: this is actually using COM interfaces registered on a remote computer. DCOM is very similar to running COM. Again a type library is required when compiling the application. For example, For Example, using Delphi:

```
var
    a: IProfile;
begin
    a := CreateremoteComobject('\\test', CLASS_Profile) as Profile;
        if a.Open['Provider=OraOLEDB.Oracle.1;Persist Security
            Info=False;User
ID=test;Data Source=tiger', 'test', 'scott', '\\test'] and
a.Authenticate[1, '', ''] then
            [...]
        a := nil;
end;
```

In this previous example, '\\test' is the host (remote) computer.

Using MTS

Any COM thread runs as a regular process, and thus is able to destabilize the host computer. MTS brings about a context that allows the machine to be shielded against COM object misbehavior. For example:

For Example, using Delphi:

```
var
    TransactionContextEx: ITransactionContextEx ;
    a: IProfile;
begin
    TransactionContextEx := CreateTransactionContextEx;
    try
        OleCheck(TransactionContextEx.CreateInstance(CLASS_Profile, IProfile, a));
            if a.Open['Provider=OraOLEDB.Oracle.1;Persist Security Info=False;User
ID=test;Data Source=tiger', 'test', 'scott', 'host'] and a.Authenticate[1, '', ''] then
            [...]
    except
        TransactionContextEx.Abort;
        raise;
    end;
    TransactionContextEx.Commit;
end;
```

3.—Management Tool User Manual

This document is a user manual for the management tool for the Adaptive Data Manager (ADM) object. It provides a guide and descriptions of all features that are part of this tool. The reader should be aware of ADM's capability before using this tool. Please consult the 'ADM COM User Manual' for in-depth information.

This tool is a utility provided to application developers and does not pretend to be an application for the end-user. This tool provides all features to manage the ADM Meta model, explore the instance data, resolve instance data locks, etc.

This tool covers eight different aspects of ADM:

Directory Security Management.

The ADM universe consists of classes of objects (facility, user group, user, meta data, meta view, application and dictionary). The 'directory' describes the relationships linking objects as privileges, thus establishing comprehensive security.

User Management.

User management consists of creating and managing users that have access rights to ADM.

Facility Management.

Facility management consists of creating and managing physical entities possibly identifying distinct data sections of ADM.

Meta Data Management.

Prior to any processing, ADM requires a Meta data model to be defined. This section of the tool manages all aspects of the Meta data model.

Meta View Management.

Any Meta model can be represented as a tree or a graph. Providing such a model does not easily enable end users to query on their own the instance data. The Meta views allow mapping of Meta data structures into one-dimensional structures, such as tables.

Instance Data Management.

Instance data is the user data that was modeled after the Meta data. For example, it is rather difficult during application development to explore the instance data in order to know whether the application was successful in inserting, updating or deleting instance data. This tool provides all means to browse and even alter the instance data.

Dictionary Management.

Application developers may create Meta data elements referring by number to a list of descriptions. The dictionary is a collection of lists, identified by a type. The type is what the Meta data element refers to. A type list is a collection of code and descriptions ordered by position. This section of the tool allows all possible management about dictionaries.

Instance Data Lock Management.

ADM allows applications to simultaneously access the same information, while allowing only one application to have modifications rights onto the instance data. This section of the tools allows for browsing and deleting locks.

Connecting to the Adaptive Data Manager

The ADM Administration tool requires all users to log in to a specific ADM data store and to authenticate themselves before access to the administrative sections. Connecting to an ADM data store requires a database connection string, a database User Name and Password. Optionally, ADM services may be hosted on a remote computer (using DCOM and MTS services), and a computer name string may be supplied into the Remote Host field. The user is required to provide an authentication: this authentication may be trusted, whereas the ADM Administration tool gathers network operating system user credentials and applies them for ADM user authentication, or explicit, whereas the user must supply a User Name and Password.

User level of privilege is recognized at user logon (by evaluating the 'directory'); the user interface of the ADM Administration tool is customized accordingly to this level.

Directory Management

Introduction

Directory management consists of establishing security and privileges among objects available in ADM. Objects are classes of resources available under ADM: these can be facility, user group, user, meta data, meta view, application and dictionary entries. A directory object entry either represents all object entries of the object class, or only one object of that object class. For example a user entry may either represent 'User J. Doe' or 'All Users'.

The directory aims to represent any possible privilege relationships among objects. Note that there may be many ways to represent the same security model.

Object Privileges are hierarchical and are organized as trees; objects located below a specific object inherit the security rights established for that specific object. Each object is assigned rights. Rights are specific by object classes; For example, rights for the User object are Create, Read, Delete and Update.

Setting the object privileges will affect this tool's user experience for all users. A user will have access to . . .

The Directory and User sections, if the current user has any of the user object rights, The Facility section, if the current user has any of the facility object rights, The Meta Data, Instance Data and Lock sections, if the current user has any of the meta data object rights, The Meta View section, if the current user has any of the meta view object rights, The Dictionary section, if the current user has any of the dictionary object rights.

Administration

Turning to FIG. 11, the Active Directory Manager is shown.

Directory Hierarchy Structure

The Directory section presents the directory structure as a tree. Clicking on the [+] symbol on the left hand side of each object expands this object to show child objects. Clicking on the [−] symbol on the left hand side collapses this object's child objects. The directory section primarily allows building the directory object hierarchy.

The following operations are possible on the object hierarchy:

Refreshing the Directory (using the context sensitive menu 'Refresh' or toolbar icon).

Saving the Directory (using the context sensitive menu 'Save' or toolbar icon).

Adding a new Facility (using the context sensitive menu 'Add Facility' or toolbar icon).

Adding a new User Group (using the context sensitive menu 'Add Group' or toolbar icon).

Adding a new User (using the context sensitive menu 'Add User' or toolbar icon).

Adding new Meta Data (using the context sensitive menu 'Add Meta Data' or toolbar icon). Note that specifying the object as a specific meta data element (as opposed to all meta data elements) is also extended to all child meta node elements of that meta node element.

Adding new Meta View (using the context sensitive menu 'Add Meta View' or toolbar icon).

Adding new Application, also sometimes referred to as Script, (using the context sensitive menu 'Add Application' or toolbar icon).

Adding new Dictionary (using the context sensitive menu 'Add Dictionary' or toolbar icon).

Deleting (using the context sensitive menu 'Delete' or toolbar icon).

Any operation on the directory is pending until it is committed to the database by Saving the directory. User interface changes will be reflected at that time.

Directory Object Properties

The right hand side the directory form shows directory object properties. The properties are The object class type, either Facility, User Group, User, Meta Data, Meta View, Script or Dictionary.

The object item, either All object of the object class type, or a specific object instance. For example, an object of type User may either represent 'User J. Doe' or 'All Users'.

The object permissions. The permission are object specific. For example, permissions for the meta data object class are Create, Read, Update and Delete. Permissions are displayed into a check list box: select permissions by check the corresponding permission check boxes.

Selecting any object properties updates the selected object as properties are selected. The profile window shows the object permissions in context with the currently logged user.

User Management

Introduction

User management consists of creating and managing users that have access rights to ADM. Note that any modification to any ADM data store entries is tagged with the current user code and a date. User management is primarily focused on tracking users and creating and maintaining authentication credential. A user is authenticated using either explicit authentication (using a user name and password) or using trusted authentication (by retrieving authentication credentials established-by the network operating system.) Note that users may have one or many trusted and/or explicit authentications. User management is the highest privilege within the ADM Administration tool. A user granted user management privilege rights is also granted management of the Directory section.

Administration

Turning to FIG. 12, the User Manager screen is shown.

The User section presents the list of users on the left hand side. Selecting a user displays user properties on the right hand side.

User properties consist of the user last and first name, an external user ID as well as an active check box. Checking off the user Active check box will disable the user: the user will no longer have access to ADM. The bottom part of the right hand side of the User section shows user authentications. This portion allows adding, editing or deleting user authentications. Add or editing a user authentication will display the following popup window:

Note that this popup window allows for entry of both trusted and explicit authentications.

Administrative Functions

The following administrative functions are available:

Refreshing User information (using the context sensitive menu 'Refresh' or toolbar icon).

Saving User information (using the context sensitive menu 'Save' or toolbar icon).

Adding a new user (using the context sensitive menu 'Add' or toolbar icon).

Deleting a user (using the context sensitive menu 'Delete' or toolbar icon).

Facility Management

Introduction

Facility management consists of creating and managing placeholders for physical entities such as corporation departments, satellite offices, etc. Using the directory, it is then possible to assign users rights and privileges under each facility. Facility management is primarily focused on creating and maintaining facility basic information. Note that a facility setup may include a preference for user's explicit or trusted authentication. This section will only appear to the user if the user is granted privilege to the 'All' Facility class of objects.

Administration

The four administration functions are refreshing the list of facilities, save changes made, and adding or deleting a facility. Facility properties consists of the facility name, the preferred user authentication type for the facility, and if the facility is active. Turning to FIG. 13, the Facility Manager screen is shown.

Administrative Functions

Refreshing the facility list (using the context sensitive menu 'Refresh' or toolbar icon).

Saving changes to the facility list (using the context sensitive menu 'Save' or toolbar icon).

Adding a facility (using the context sensitive menu 'Add Facility' or toolbar icon).

Deleting a facility (using the context sensitive menu 'Delete Facility' or toolbar icon).

Meta Data Management

Introduction

Meta data represents the definition of the data that will be collected. In other words, the Meta data defines the shapes and attributes of the instance data and prepares the database for receiving the end user's application data. For more information about Meta Data, refer to the ADM COM User Manual document, 'Data Store Model' Section.

Administration

Meta data administration is granted to the current user if the user has privileges on the 'All' Meta Data Class of objects.

There is only one Meta data model per ADM data store (i.e. database user.) Meta data is organized as a tree. There can be several Meta data roots to the Meta data model. Turning to FIG. 14, the Meta Data Manager is shown with a 'PROVIDER' root.

The tool allows for Meta data elements to be browsed, added and removed. Browsing the Meta data set is done using the left-hand side (tree view) field by clicking on the [+] or [−] bitmaps, or by double-clicking on the Meta element names. All attributes for a Meta element are shown on the right hand side. Modifying attributes does not alter the database immediately. Changes are only submitted to the database when 'saving' the Meta data to the database. Note that the Meta data model can be refreshed (i.e. re-read) from the database. If the Meta data was in a modified state, the user is prompted to save or ignore changes prior to refreshing the Meta data display. Only Meta elements that have been changed are saved to the database. Notes that are deleted from the Meta model are in fact 'archived'. The Meta data is still present but no longer displayed to the user. Note that the list of data types is hard coded to the application and thus cannot be changed. The list of flags is based on a system dictionary list, and is set by default at system installation. The icon on the left hand side of each meta data element visually indicates the data type of the element. Possible icons are:

Icon Data type Name Description

0

Container The Container data type is to provide a logical meta data group to child meta data elements.

1
String A String data type allows storage of character strings up to 255 characters.
2
Integer The Integer data type is a signed 32-bit integer, ranging from −2147483648 to 2147483647.
3
Real number The Real data type is a number storing values ranging from $5.0 \times 10^{-324}$ to $1.7 \times 10^{308}$.
4
Date The Date data type is used to hold date and time values.
5
Long String The Long String data type allows storage of strings up to 4294967294 characters. This data type is slower to handle than the String data type.
6
Boolean The Boolean data type holds TRUE or FALSE values.
7
Array The Array data type is very similar to the Container data type, as it provides a logical meta data group to child meta data elements. As opposed to the Container data type, the Array data type may have none or many child array records of child meta data elements.
9
Virtual Array The Virtual Array data type allows the creation of arrays with child elements belonging to another Array data type meta element. When creating the Virtual Array meta element, another Array meta element has to be selected.

Administrative Functions

All Meta element operations are effective by selecting a Meta element on the left-hand side, and either Selecting an operation by clicking on the button tool bar or right clicking on the Meta element and choosing the operation from the context sensitive menu, or
 Modifying Meta element attributes and properties on the right-hand side of the screen.

Possible operations are:

Saving the Meta Model (using the context sensitive menu 'Save' or toolbar icon).
 All Meta data is saved, and all data is marked as 'not modified' again.
 Importing the Meta Model from an XML file (using the context sensitive menu 'Import' or toolbar icon). Refer to the 'XML Operations' section.
 Exporting the Meta Model to an XML file (using the context sensitive menu 'Export' or toolbar icon). Refer to the 'XML Operations' section.
 Adding a Meta data sibling (using the context sensitive menu 'Add Meta Data Sibling' or toolbar icon). In other words, a new Meta element is added at the same level of the Meta element currently selected. The parent Meta data is flagged as modified, and the user must save the Meta data before the Meta data model change is effective.
 Adding a Meta data Child (using the context sensitive menu 'Add Meta Data Child' or toolbar icon). In other words, a new Meta element is added as a child of the currently selected Meta element. The parent Meta data is flagged as modified, and the user must save the Meta data before the Meta data model change is effective.
 Deleting the currently selected Meta element (using the context sensitive menu 'Delete Meta Data' or toolbar icon). The parent Meta data is flagged as modified, and the user must save the Meta data before the Meta data model change is effective.
 Expanding the currently selected Meta element (using the context sensitive menu 'Expand All' or toolbar icon). In other words, all Meta children of the currently selected Meta element are displayed.
 Collapsing the currently selected Meta element (using the context sensitive menu 'Expand All' or toolbar icon). In other words, all Meta children of the currently selected Meta element are not displayed.
 Cutting the current Meta element and all child Meta elements to the clipboard (using the context sensitive menu 'Cut' or toolbar icon).
 Copying the current Meta element and all child Meta elements to the clipboard (using the context sensitive menu 'Copy' or toolbar icon.) The parent Meta data is flagged as modified, and the user must save the Meta data before the Meta data model change is effective.
 Pasting Meta elements from the clipboard to the currently selected Meta element (using the context sensitive menu 'Paste' or toolbar icon.) The parent Meta data is flagged as modified, and the user must save the Meta data before the Meta data model change is effective.

Additional operations are:

Refreshing the Meta data model display by using the context sensitive menu 'Refresh' or toolbar icon.
 Searching for a string in the Meta data by using the toolbar icon.
 Finding the next item in the Meta data for the search that was previously performed by using the toolbar icon.
 Closing the application when data has been modified will prompt the user to save the changes and close the application, ignore the changes and close the application, or cancel closing the application.

XML Operations

Importing Meta Data

Meta data can be created by importing a Meta data XML export file.

To start this operation, use the context sensitive menu 'Import' or click on the toolbar icon. Two options are available:

Insert at selected Meta data.

The Meta data input is read, and the new Meta data elements are inserted at the current location as children of the currently selected Meta element. This operation may fail if any imported Meta element name is identical to any of the existing Meta element name elsewhere in the model.

Create an entirely new Meta data branch.

The Meta data input is read and an entirely new Meta model branch is created. This operation may fail if an imported Meta data name corresponds to an existing Meta data element name present elsewhere in the Meta data model.

The new Meta model will apply to the database only when saved. If the Import operation fails, the Meta model is not affected by any of the Import operation.

Exporting Meta Data

The Meta data model can be exported as an XML file by using the context sensitive menu 'Export' or the toolbar icon.

Two options are available:

Export at selected Meta data.

The current Meta data branch is exported as an XML file.

Export all Meta data.

All Meta data elements are exported into a single XML output file.

Meta View Management

Introduction

Meta Views allow for Meta data elements to be gathered into a single structure called a Meta View. Whenever Instance data is inserted, corresponding to any the Meta data definitions, then the Meta View is updated to reflect the instance Data State. In other words, Meta Views are one-level collections of Meta data elements.

Administration

Meta View administration is granted to the current user if the user has privileges on the 'All' Meta View Class of objects.

Turning to FIG. 15, the Meta View Manager screen is shown.

Expanding a Meta View on the left-hand side, by either clicking on the [+] icon or double-clicking on the Meta View name, will show all Meta Data elements that are part of the Meta View.

Selecting a Meta View name on the left-hand side allows the Meta View name to be modifiable on the right-hand side. Selecting a Meta View element on the left-hand side allows the Meta View element name to be renamed, and possibly a different Meta element to be selected. Any element of the Meta view can be removed. A new Meta View element can be added at any time.

Modifying Meta View attributes does not modify the database right away. Changes are only submitted to the database when 'saving' the Meta View data to the database. Note that the Meta View data model can be refreshed (i.e. re-read) from the database if the Meta View data is in a modified state. The user is then prompted to save or ignore changes, prior to refreshing the Meta View data display. Only Meta View elements that have been changed are saved to the database.

All Meta View element operations are effective by selecting a Meta View element on the left-hand side, and either Selecting an operation by clicking on the button tool bar or right clicking on the Meta View element and choosing the operation from the context sensitive menu, or Modifying Meta View element attributes and properties on the right-hand side of the screen.

Possible operations are:

Refreshing the Meta View Model (using the context sensitive menu 'Refresh' or toolbar icon).

Saving the Meta View Model (using the context sensitive menu 'Save' or toolbar icon).

All Meta View data is saved, and all data is marked as 'not modified' again.

Importing the Meta View Model from an XML file (using the context sensitive menu 'Import' or toolbar icon). Refer to the 'XML Operations' section.

Exporting the Meta View Model to an XML file (using the context sensitive menu 'Export' or toolbar icon). Refer to the 'XML Operations' section.

Adding a new Meta View (using the context sensitive menu 'Add View' or toolbar icon). The element is flagged as modified, and the user must save the Meta View before the Meta View model change is effective.

Note that the Meta View name cannot be any of these reserved keywords: AUTHENTICATION, AUTHENTICATION_ARC, AUTHENTICATION_SEQ, DATA_IN_PROCESS, DATA_PROCESSOR, DATA_PROCESSOR_SEQ, DICTIONARY_GROUP, DICTIONARY_GROUP_ARC, DICTIONARY_ITEM, DICTIONARY_ITEM_ARC, DIRECTORY, DIRECTORY_ARC, DIRECTORY_SEQ, FACILITY, FACILITY_ARC, FACILITY_SEQ, META_APPLICATION, META_APPLICATION_ARC, META_APPLICATION_SEQ, META_NODE, META_NODE_ARC, META_NODE_EDGE, META_NODE_SEQ, META_VIEW, META_VIEW_COLUMN, META_VIEW_LOG, META_VIEW_SEQ, NODE, NODE_ARC, NODE_EDGE, NODE_LOCK, NODE_SEQ, NODE_WORD_INDEX, SEQUENCE_GENERATOR, SYSTEM_USER, SYSTEM_USER_ARC, SYSTEM_USER_EVENT, SYSTEM_USER_EVENT_SEQ, SYSTEM_USER_GROUP, SYSTEM_USER_SEQ Adding a new Meta View Column (using the context sensitive menu 'Add View Column' or toolbar icon). In other words, a new Meta View column is added as a child of the currently selected Meta View element. The Meta View element is flagged as modified, and the user must save the Meta View elements before the Meta View model change is effective.

Deleting a Meta View or Column (using the context sensitive menu 'Delete View' or toolbar icon). The Meta View element is flagged as modified, and the user must save the Meta View elements before the Meta View model change is effective.

Expanding the current Meta View elements (using the toolbar icon).

Collapsing the current Meta View elements (using the toolbar icon).

Cutting the current Meta View element to the clipboard (using the context sensitive menu 'Cut' or toolbar icon).

Copying the current Meta View element to the clipboard (using the context sensitive menu 'Copy' or toolbar icon). The user must save the Meta View elements before the changes are effective.

Pasting Meta View elements from the clipboard (using the context sensitive menu 'Paste' or toolbar icon). The user must save the Meta Views before the Meta View model change is effective.

Displaying the corresponding Meta Element from a Meta View column element (using the context sensitive menu 'Meta Element' or toolbar icon).

Closing the application when data has been modified will prompt the user to save the changes and close the application, ignore the changes and close the application, or cancel closing the application.

Interactions with the View Services

The basic purpose of the Meta View section is to prepare and manage Meta view data for the multiple view services. The log of activity is visible on the right hand side of the Meta view form in the Activity Log panel, by selecting a Meta View name on the left hand side panel. Right clicking on the left or right hand side panels allows several operations to interact with the background views services:

Refresh Log (Left hand-side panel) or Refresh (Activity Log panel):

This command allows the activity log content to be refreshed. Note that this content is also refreshed with selecting a different Meta view.

Clear (Activity Log panel only):

This command allows clearing the activity log for a specific Meta view.

Force Creation (Left hand-side panel and Activity Log panel):

This command forces the view services to recreate a view from the Meta view definition. This command is especially useful when a view creation previously failed due to the presence of a non-numeric character inside a numeric field such as a date, integer or floating-point field for example. Further refreshing the log will display real-time activity of the view service recomposing the view.

XML Operations

Importing Meta View Data

Meta Views can be created by importing a Meta View export XML file. To start this operation, use the context sensitive menu 'Import' or click on the toolbar icon. A Meta View export file may have one or many Meta View definitions. The new Meta views will only apply to the database when saved. If the Import operation fails, then the Meta model is not affected by any of the Import operation.

Exporting Meta View Data

The Meta views can be exported as an XML file by using the context sensitive menu 'Export' or the toolbar icon.
Two options are available:
Export selected Meta View.
The current Meta view is exported as an XML file.
Export all Meta Views.
All Meta Views are exported into a single XML output file.

Instance Data Management

Turning to FIG. 16, the Instance Data Manager screen is shown.

Instance data consists of application user data shaped after the corresponding Meta data. In other words, instance data is the instantiation of the Meta data. For more information about Meta Data and Instance data, refer to the ADM COM User Manual document, 'Data Store Model' Section.

Instance Data administration is granted to the current user if the user has privileges on the 'All' Meta Data Class of objects.

Administration

The Instance data management tool has been built to emulate features from Microsoft Explorer. The desktop view presents two panes, the left one exclusively for navigation, and the right one for navigation and displaying instance data values. The left-hand side tree view style object only presents instance data of data type Container, Array or Virtual Array, thus enabling the display of the data tree. The right-hand side list view object presents three types of information:

- Instance data discrete values: These instance data elements are the children of the instance data element selected on the left-hand side. These elements' data types are string, integer, Boolean, date, and realdata types. Double-clicking on the instance data, or using the context sensitive menu 'Open' can modify this value.
- Instance data array data values: These instance data elements are also the children of the instance data element selected on the left-hand side, but allow for further navigation into the instance data tree. Double-clicking on the instance data entry, or using the context sensitive menu 'Open' can expand this value.
- The default value, as the instance data value the instance data element selected on the left-hand side. This value can be modified by either double-clicking on the list view 'default value' value, or by using the context sensitive menu 'Open'. Several operations are possible on all instance data elements by selecting an instance data element, and selecting an operation by clicking on the button tool bar or by right clicking on the instance data element and choosing the operation from the context sensitive menu.

Possible operations are:

- Refreshing the current instance data display by either using the context sensitive menu 'Refresh' or toolbar icon.
- Deleting the currently selected instance data element (either using the context sensitive menu 'Delete' or toolbar icon). AFTER ANSWERING "Yes" TO "Delete Node 'x' and child nodes?", ALL CORRESPONDING INSTANCE DATA IS IMMEDIATELY DELETED. THERE IS NO POSSIBLE UNDO OPERATION.
- Import instance data from an XML file (either using the context sensitive menu 'Import' or toolbar icon). Refer to the 'XML Operations' section.
- Export Instance data to an XML file (either using the context sensitive menu 'Export' or toolbar icon). Refer to the 'XML Operations' section.
- Navigate to the instance data's Meta data.
- This feature provides the ability to navigate to the Meta data in the Meta Data form, either using the context sensitive menu 'View Meta Data' or toolbar icon.
- Search for Instance data.
- This feature provides the ability to search instance data that has been flagged for the Index interface search engine. Refer to the 'Searching the instance data' section.

Searching the Instance Data

Some Meta data elements may be flagged as 'indexed'. For example, in the case of a newspaper article having an author, a headline, a date, a story and a title, all authors, title and story will be flagged as 'Free Text Index', while the article (meta data parent of previously mentioned meta data elements) will be the 'Index result'. If the result of a search query presents itself of a hit on an article title, then the article itself (i.e. the 'Index result') is the result of the query, and will be returned as such to the user.

Searches can be done either on a portion of the instance data, or on the whole instance data. Clicking on the icon, will bring about the following window:

This window allows one to either search starting at the previously selected instance data object, or to perform a global search. The search can include many words: the search will be equivalent to 'Word#1 AND Word#2 AND Word#3 . . . ' Note that the search may also be broadened to a Soundex search.

After pressing 'Search', and if the search is unsuccessful, a message is presented to the user announcing that 'No instance data was found having "x"'. If at least one instance data is found, the window is dismissed and this instance data is opened and presented as selected to the user.

The top of the instance data tool also presents the number of query results, as well as left and right arrows for navigating from one query result to the next query result.

XML Operations

Importing Instance Data

Instance data can be imported from an export XML file. To start this operation, use the context sensitive menu 'Import' or click on the toolbar icon.

This dialog box requires an existing XML file to be selected. It also requires specifying if the imported instance data should be created as a new instance data tree, merged or appended to the currently selected instance data. Note that the instance data may contain instantiation of Meta elements not present into the current Meta model. The 'Modify Meta Data Model as needed' check box allows for such extension.

Exporting Instance Data

Instance data can be exported to an XML file. To start this operation, use the context sensitive menu 'Export' or click on the toolbar icon. Instance data is exported, beginning where the user had currently selected instance data.

Dictionary Management

Introduction

The Dictionary concept is a remnant from relational database structures. Most data inserted into relational database is coded and only the description is shown to the user. If a codified element description is changed, the element codification is not affected and any table relationships are still valid.

The same concept applies for Meta Data-based structures. While the emphasis is not necessarily on table relationships, the ability to code a fixed data set and to only store the coded value is important. The Meta data structure puts an emphasis on the end-user application for displaying dictionary lists, and providing back to ADM codified values. Dictionary entries are identified with dictionary type, ID and description. The dictionary type identifies the dictionary group. A group is a collection of dictionary items of the same type. Items are ordered with a position, thus allowing the display to be changed for user convenience.

Administration

The Dictionary administration tool is the seventh icon button of the ADM administration tool. The tool will show on the left-hand side all dictionary groups that have been already defined. Note that ADM defines by default one dictionary group, 'USER_GROUP', for management of the Meta data.

Turning to FIG. 17, the Dictionary Manager screen is shown.

Expanding a dictionary group on the left-hand side, by clicking on the [+] icon or double-clicking on the dictionary groups title, will show all dictionary items that are part of the dictionary group.

Selecting a dictionary group or dictionary item on the left-hand side allows the element to be modifiable on the right-hand side. Selecting a dictionary group element will display the element ID, administration level, numeric-only flag, active flag and description. Selecting a dictionary item element will display the element ID, administration level, numeric-only flag, active flag and description as well, with a larger description field available.

Modifying dictionary attributes does not modify the database immediately. Changes are only submitted to the database when 'saving' the dictionary data to the database. Note that the dictionary data can be refreshed (i.e. re-read) from the database. If the dictionary data was in a modified state, then the user is prompted to save or ignore changes, prior to refreshing the dictionary data display. Only dictionary elements that have been changed are saved to the database.

All dictionary element operations are effective by selecting a dictionary element on the left-hand side, and either Selecting an operation by clicking on the button tool bar or by right clicking on the dictionary element and choosing the operation from the context sensitive menu, or Modifying dictionary element attributes and properties on the right-hand side of the screen.

Possible operations are:

Saving the dictionary data (using the context sensitive menu 'Save' or toolbar icon). All dictionary data is saved, and all data is marked as 'not modified' again.

Importing dictionary data from an XML file (using the context sensitive menu 'Import' or toolbar icon). Refer to the 'XML Operations' section.

Exporting the dictionary data to an XML file (using the context sensitive menu 'Export' or toolbar icon). Refer to the 'XML Operations' section.

Auto-ordering dictionary items for the current dictionary group (using the context sensitive menu 'Auto Order' or toolbar icon).

Adding a new dictionary group (using the context sensitive menu 'Add Group' or toolbar icon). The user must save the dictionary elements before the changes are effective.

Adding a new dictionary item (using the context sensitive menu 'Add Item' or toolbar icon). The user must save the dictionary elements before the changes are effective.

Deleting a dictionary element (using the context sensitive menu 'Delete Item' or toolbar icon). The user must save the dictionary elements before the changes are effective.

Cutting to the clipboard the current dictionary element (using the context sensitive menu 'Cut' or toolbar icon). The user must save the dictionary elements before the changes are effective.

Copying to the clipboard the current dictionary element (using the context sensitive menu 'Copy' or toolbar icon). The user must save the dictionary elements before the changes are effective.

Pasting from the clipboard dictionary elements (using the context sensitive menu 'Paste' or toolbar icon). The user must save the dictionary elements before the changes are effective.

Additional operations are:

Refreshing the dictionary display by using the context sensitive menu 'Refresh' or toolbar icon.

Closing the application when data has been modified will prompt the user to save the changes and close the application, ignore the changes and close the application, or cancel closing the application.

XML Operations

Importing Dictionary Data

Dictionaries can be created by importing a dictionary export XML file. To start this operation, use the context sensitive menu 'Import' or click on the toolbar icon. A dictionary export file may have one or many dictionary group definitions. The new dictionary will only apply to the database when saved. If the Import operation fails, the dictionary model is not affected by any of the Import operation.

Exporting Dictionary Data

The dictionary data can be exported as an XML file by using the context sensitive menu 'Export' or using the toolbar icon.

Two options are available:

Export selected Dictionary Group.

The current dictionary is exported as an XML file.

Export all Dictionary Groups.

All dictionary groups are exported into a single XML output file.

Instance Data Lock Management

Introduction

An instance data lock is the means to grant exclusive (Read & Write) data access to one user while any other users have read-only access to the same data. Locks are structures requested by end-user applications. By default, all data is accessed in read-only mode. Setting a lock on a particular instance data node will grant exclusive access to this instance data node AS WELL AS ALL CHILD INSTANCE DATA NODE OF THAT NODE. Therefore, one needs only one lock to grant access to many instance data elements. This ability must be weighted against being able to grant many users concurrent instance data elements. Most of the possibility of concurrent data access lies on a correctly object oriented design, expressed in terms of Meta data design.

Locks consist of an instance data reference, a date when the lock was set, a lock owner, a session number, and the machine that placed the lock. The session guarantees that the same user (owner) may place several locks under different application sessions without conflicts.

Access to this section is granted to user having privileges on Meta Data management.

Administration

Turning to FIG. 18, the Instance Data Lock Manager screen is shown.

By selecting a specific lock entry, the tool provides four basic features:

Refresh the list of locks.

Using the context sensitive menu 'Refresh' or toolbar icon can refresh (i.e. re-load) the list of current locks.

Delete a lock.

Using the context sensitive menu 'Delete Group', or toolbar icon can delete the selected lock. Note that this action can seriously hinder any currently active application making reference to the corresponding instance data. This tool feature should be used with care and consideration.

Navigate to the lock instance data.

This feature provides the ability to navigate to the instance data in the Instance Data form, using the context sensitive menu 'View Instance Data' or toolbar icon.

Navigate to the lock Meta data.

This feature provides the ability to navigate to the Meta data in the Meta Data form, using the context sensitive menu 'View Meta Data' or toolbar icon.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

What is claimed is:

1. A method for managing an information storage infrastructure and a flexible development environment for data storage using a computer system, comprising:
    managing system resources including a relational database;
    authenticating and selectively providing access to users through predetermined user roles;
    creating a metadata model for organizing instance data having metadata elements and relationships among the elements, wherein the metadata model is represented using trees and graphs in a table driven infrastructure;
    running processes and generating said instance data;
    storing the instance data, using said metadata model, in a plurality of tables having said table driven infrastructure within said relational database;
    performing transforms of the instance data, comprising rendering said instance data into at least one view; and
    keeping an audit trail of changes to said instance data.

2. A method in accordance with claim 1, wherein said authenticating comprises managing access to the data by authenticating users through several levels of authentication.

3. A method in accordance with claim 1, further comprising optimizing the metadata model by structuring the trees and graphs in the relational database.

4. A method in accordance with claim 3, wherein said step of optimizing the metadata model comprises using a plurality of concurrent metadata model trees with corresponding instance data trees in the same database.

5. A method in accordance with claim 1, further comprising defining parent-child relationships among a plurality of said metadata elements.

6. A method in accordance with claim 1, further comprising modifying the metadata model and deploying said modified metadata model.

7. A method in accordance with claim 6, wherein said step of modifying the metadata model comprises one of the steps of adding, editing, and deleting a metadata element.

8. A method in accordance with claim 1, wherein said keeping an audit trail step comprises tracking changes to instance data with user, date, and data value information.

9. A method in accordance with claim 1, further comprising providing for import and export of said metadata elements and said instance data using extensible mark-up language.

10. A method in accordance with claim 1, wherein said step of performing transforms of the instance data comprises:
    selecting a view;
    processing said view using a relational database table; and
    allowing access of said view with a SQL enabled tool.

11. A method in accordance with claim 1, wherein said step of storing the instance data comprises managing relationships among said instance data in a set of tables.

12. A method in accordance with claim 1, wherein said step of storing the instance data comprises storing the instance data in XML format within said relational database.

13. A method in accordance with claim 1, wherein said step of authenticating and selectively providing access to users through predetermined user roles comprises using security features provided by said method for managing an information storage infrastructure and said relational database to define user rights and privileges.

14. A method in accordance with claim 1, wherein said step of performing transforms of the instance data comprises displaying said view using forms.

15. A method in accordance with claim 14, wherein said rendering step comprises using forms created by a compiled application.

16. A method in accordance with claim 1, wherein said step of storing the instance data in a plurality of tables comprises allowing a first user to modify instance data while allowing a second user to modify the same instance data.

17. A method in accordance with claim 1, further comprising processing user requests to modify instance data using rules governing relationships among the instance data.

18. A method in accordance with claim 1, further comprising managing work flow in an enterprise.

19. A method in accordance with claim 18, wherein the step of managing work flow in an enterprise comprises the steps of:
    managing scheduling data;
    managing laboratory report data;
    managing immunization data;
    managing insurance data;
    managing billing data;
    managing medical record data; and
    modifying said instance data to reflect changes.

20. A method for managing instance data, comprising:
    defining a metadata model establishing metadata elements and a table driven infrastructure for storing the instance data, said instance data organized according to said metadata model;
    storing said metadata and said instance data in a relational database,
    altering said metadata model when necessary without requiring reorganization or substantial manipulation of said instance data,
    creating a user interface,
    managing access to said instance data by users based on a security scheme,
    said managing including allowing authorized users to modify said instance data using a computer through said user interface.

21. A method in accordance with claim 20, wherein said step of managing access to said instance data comprises authenticating users through several levels of authentication describing user rights.

22. A method in accordance with claim 20, wherein said step of managing access to said instance data comprises at least one of the steps of retrieving, viewing, adding, and deleting instance data.

23. A method in accordance with claim 20, wherein said step of defining a metadata model comprises establishing relationships among the metadata elements using trees and graphs.

24. A method in accordance with claim 20, wherein said step of managing access to said instance data comprises processing user requests to modify instance data using a rule engine that includes a set of rules governing relationships among various parts of the instance data.

25. A method of managing electronic records, comprising:
   storing data on a relational database, comprising modeling processes to create a metadata model establishing metadata elements and relationships among the elements and storing instance data following the metadata model;
   running an application server;
   authenticating and selectively providing access to users through a directory describing predetermined user rights;
   rendering instance data from said relational database,
   allowing users to modify said instance data stored on said relational database.

26. A method in accordance with claim 25, wherein said authenticating comprises managing access to the data by authenticating users through several levels of authentication.

27. A method in accordance with claim 25, wherein said running an application server comprises:
   running algorithms for one of the steps of data management, data access, business management and concurrency management;
   processing user requests to modify instance data using a rule engine that includes a set of rules governing relationships among various parts of the instance data;
   providing means for said users to establish connections to said relational database.

* * * * *